(12) United States Patent
Youngman

(10) Patent No.: US 9,175,000 B2
(45) Date of Patent: Nov. 3, 2015

(54) BUPRENORPHINE ANALOGS

(71) Applicant: Purdue Pharma L.P., Stamford, CT (US)

(72) Inventor: Mark A. Youngman, North Wales, PA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 14/096,311

(22) Filed: Dec. 4, 2013

(65) Prior Publication Data

US 2014/0163058 A1 Jun. 12, 2014

Related U.S. Application Data

(60) Provisional application No. 61/734,828, filed on Dec. 7, 2012.

(51) Int. Cl.
*A61K 31/485* (2006.01)
*C07D 489/12* (2006.01)

(52) U.S. Cl.
CPC .................................. *C07D 489/12* (2013.01)

(58) Field of Classification Search
USPC .............................................. 514/279; 546/39
See application file for complete search history.

(56) References Cited

U.S. PATENT DOCUMENTS 3,433,791 A * 3/1969 Bentley ............................. 546/39
3,464,994 A 9/1969 Bentley et al.
(Continued)

FOREIGN PATENT DOCUMENTS

| WO | 2010014229 A1 | 2/2010 |
| WO | 2012/038813 A1 | 3/2012 |
| WO | WO-2013/167963 A1 | 11/2013 |

OTHER PUBLICATIONS

Rennison, et al. "Cinnamoyl derivatives of 7-alpha-aminomethyl-6,14-endo-ethanotetrahydrothebaine and 7-alpha-aminomethyl-6,14-endo-ethanotetrahydrooripavine and related opioid ligands." Journal of Medicinal Chemistry, vol. 50, No. 21, 2007, pp. 5176-5182.

Derrick, et al. "Cinnamoyl derivatives of 7-alpha-amino- and 7-alpha-(aminomethyl)-N-(cyclopropylmethyl)-6,14-endo-ethanotetrahydronororipaavines are high-potency opioid antagonists." Helvetica Chimica Acta, vol. 83, 2000, pp. 3122-3130.

(Continued)

*Primary Examiner* — Charanjit Aulakh
(74) *Attorney, Agent, or Firm* — Purdue Pharma L.P.; Alan L. Koller; Weiying Yang

(57) ABSTRACT

The present invention is directed to Buprenorphine Analog compounds of the Formula I, Formula II, Formula III, Formula IV, and Formula V, wherein $R^1$, $R^2$, $R^{3a}$, $R^{3b}$, $R^{15a}$, $R^{15b}$, X, Q, G, and Y are as defined herein.

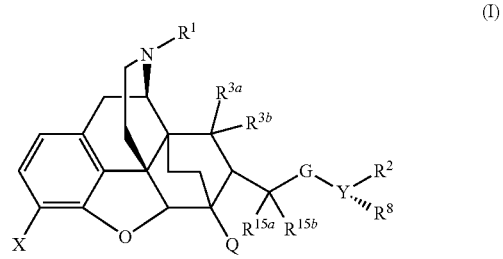

(I)

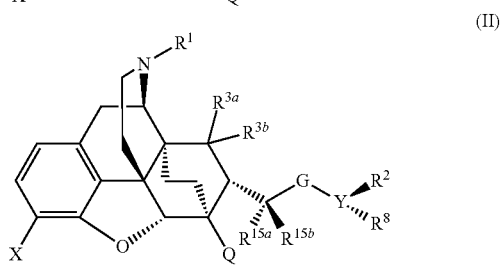

(II)

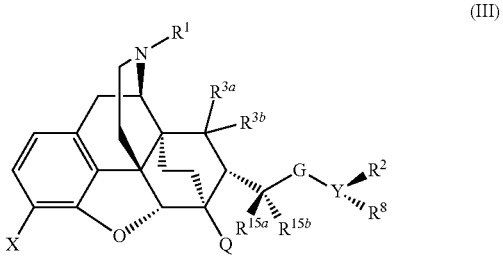

(III)

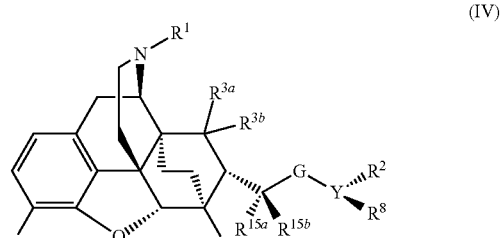

(IV)

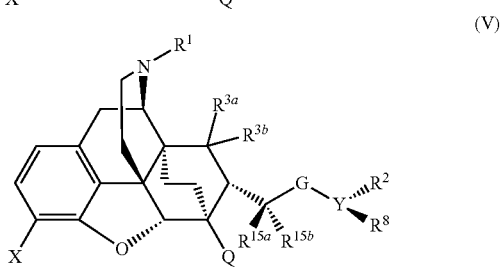

(V)

Compounds of the Invention are useful for treating pain and other conditions modulated by activity of opioid receptors.

47 Claims, No Drawings

(56) References Cited

U.S. PATENT DOCUMENTS

| | | |
|---|---|---|
| 6,740,641 B2 | 5/2004 | Gao et al. |
| 6,823,205 B1 | 11/2004 | Jara |
| 6,958,398 B1 | 10/2005 | Kupper et al. |
| 7,084,150 B2 | 8/2006 | Boer et al. |
| 7,125,884 B2 | 10/2006 | Reidenberg et al. |
| 7,202,259 B2 | 4/2007 | Chen |
| 7,687,518 B2 | 3/2010 | Chen |
| 8,026,254 B2 | 9/2011 | Chen |
| 8,426,594 B2 | 4/2013 | Kyle |
| 8,481,743 B2 | 7/2013 | Zhou |
| 8,530,494 B2 | 9/2013 | Kyle et al. |
| 8,937,084 B2 | 1/2015 | Park et al. |
| 8,946,255 B2 | 2/2015 | Kassick et al. |
| 8,957,084 B2 | 2/2015 | Kyle et al. |
| 8,969,358 B2 | 3/2015 | Goehring et al. |
| 8,980,906 B2 | 3/2015 | Tafesse |
| 8,987,287 B2 | 3/2015 | Goehring et al. |
| 2005/0192308 A1 | 9/2005 | Gale et al. |
| 2014/0057931 A1 | 2/2014 | Kyle et al. |
| 2014/0057932 A1 | 2/2014 | Reisch |
| 2014/0135351 A1 | 5/2014 | Lockman et al. |
| 2014/0221419 A1 | 8/2014 | Lockman et al. |
| 2014/0275117 A1 | 9/2014 | Goehring et al. |
| 2014/0364448 A1 | 12/2014 | Kyle |

OTHER PUBLICATIONS

Bentley, et al. "Novel analgesics and molecular rearrangements in the morphine-thebaine group. Part VIII. 7-alkyl-6,14-endo-ethenotetrahydrothebaine and related compounds." J. Chem. Soc., 1969, pp. 826-830.

K.M. Foley, Pain, in Cecil Textbook of Medicine 100-107, J.C. Bennett and F. Plum eds., 20th ed. 1996.

D. Barlocco et al., "The opioid-receptor-like 1 (ORL-1) as a potential target for new analgesics." Eur. J. Med. Chem., 2000, 35:275.

J.S. Mogil et al., "Orphanin FQ is a functional anti-opioid peptide." Neurosci., 1996, 75:333.

K. Lutfy et al., "Tolerance develops to the inhibitory effect of orphanin FQ on morphine-induced antinociception in the rat." NeuroReport, 1999, 10:103.

M.M. Morgan et al., "Antinociception mediated by the periaqueductal gray is attenuated by orphanin FQ." NeuroReport, 1997, 8:3431.

J. Tian et al., "Involvement of endogenous Orphanin FQ in electroacupuncture—induced analgesia," NeuroReport, 1997, 8:497.

J. Tian et al., "Functional studies using antibodies against orphanin FQ/nociceptin," Peptides, 2000, 21:1047.

H. Ueda et al., "Enhanced Spinal Nociceptin Receptor Expression Develops Morphine Tolerance and Dependence," J. Neurosci., 2000, 20:7640.

Wood & Galligan, "Function of opioids in the enteric nervous system," Neurogastroenterology & Motility, 2004, 16 (Suppl.2): 17-28.

K. Lufty et al., "Buprenorphine-induced antinociception is mediated by µ-opioid receptors and compromised by concomitant activation of opioid receptor-like receptors." J. Neurosci., 2003, 23:10331-10337.

Pergolizzi et al.,Opioids and the Management of Chronic Severe Pain in the Elderly: Consensus Statement of an International Expert Panel with Focus on the Six Clinically Most Often Used World Health Organization step IB Opioids (buprenorphine, Fentanyl, Hydromorphone, Methadone, Morphine, Oxycodone. Pain Practice, 2008, 8(4): 287-313).

Tzchentike, Behavioral pharmacology of buprenorphine, with a focus on preclinical models of reward and addiction. Psychopharmacology, 2002, 161: 1-16.

International Search Report mailed Feb. 17, 2014 in corresponding International Application No. PCT/IB2013/002705 and Written Opinions.

S. Wnendt et al., "Agonistic effect of buprenorphine in a nociceptin/OFQ receptor-triggered reporter gene assay." Molec. Pharmacol., 1999, 56:334-338.

Hawkinson et al., Opioid activity profiles indicate similarities between the nociceptin/orphanin FQ and opioid receptors. Eur. J. Pharmacol, 2000, 389:107-114.

Gutstein and Akil, "Opioid Analgesics," Goodman & Gilman's The Pharmacological Basis of Therapeutics, 547-590, Chapter 21, 11th Ed. 2004.

\* cited by examiner

BUPRENORPHINE ANALOGS

This application claims the benefit of U.S. Provisional Application Ser. No. 61/734,823, filed Dec. 7, 2012.

The invention is in the field of medicinal chemistry. It relates to novel buprenorphine analogs having activity as opioid receptor agonists and/or antagonists. In certain embodiments compounds of the invention have dual activity as μ, δ, and/or κ opioid agonists and ORL-1 receptor antagonists.

BACKGROUND OF THE INVENTION

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone or oxymorphone).

Although the term "narcotic" is often used to refer to opioids, the term is not specifically applicable to opioids. The term "narcotic", derived from the Greek word for "stupor", originally referred to any drug that induced sleep, only later being associated with opioids (Gutstein, Howard B., Akil, Huda, "Chapter 21. Opioid Analgesics" (Chapter 21), Brunton, L L, Lazo, J S, Parker, Kl: Goodman & Gilman's The Pharmacological Basis of Therapeutics, 11$^{th}$ Edition: http://www.accessmedicine.com/contentaspx?aID=940653). In the legal context, the term "narcotic" refers to a variety of mechanistically unrelated substances with abuse or addictive potential (Gutstein, Howard B., Akil, Huda, "Chapter 21. Opioid Analgesics" (Chapter 21), Brunton L L, Lazo J S, Parker K I: Goodman & Gilman's The Pharmacological Basis of Therapeutics, 11$^{th}$ Edition: http://www.accessmedicine.com/content.aspx?aID=940653). Thus, the term "narcotic" not only refers to opioids, but also refers to such drugs as cocaine, methamphetamine, ecstasy, etc., which exert their pharmacological effects via different receptors than opioids. Furthermore, because the term "narcotic" refers to such a wide variety of unrelated drugs, many of which do not possess analgesic properties, it cannot be assumed that a drug that has "narcotic" properties is necessarily analgesic. For example, drugs such as ecstasy and methamphetamine are not analgesic, and are not used to treat pain.

Until recently, there was evidence of three major classes of opioid receptors in the central nervous system (CNS), with each class having subtype receptors. These receptor classes are known as μ, δ and κ. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This more recently discovered receptor was classified as an opioid receptor based only on structural grounds, as the receptor did not exhibit pharmacological homology. It was initially demonstrated that non-selective ligands having a high affinity for μ, δ and κ receptors had low affinity for the ORL-1 receptor. This characteristic, along with the fact that an endogenous ligand had not yet been discovered, led to the ORL-1 receptor being designated as an "orphan receptor".

The discovery of the ORL-1 receptor and its endogenous ligand, nociceptin (also known as orphanin FQ (OFQ)) presents an opportunity for the discovery of novel compounds that can be administered for pain management or other syndromes influenced by this receptor.

Many publications in the ORL-1/nociceptin field provide evidence that activation of ORL-1 receptors in the brain can inhibit opioid-mediated analgesia (e.g., D. Barlocco et al., "The opioid-receptor-like 1 (ORL-1) as a potential target for new analgesics." *Eur. J. Med. Chem.*, 2000, 35:275; J. S. Mogil et al., "Orphanin FQ is a functional anti-opioid peptide." *Neurosci.*, 1996, 75:333; K. Lutfy et al., "Tolerance develops to the inhibitory effect of orphanin FQ on morphine-induced antinociception in the rat." *NeuroReport*, 1999, 10:103; M. M. Morgan et al., "Antinociception mediated by the periaqueductal gray is attenuated by orphanin FQ." *NeuroReport*, 1997, 8:3431; and J. Tian et al., "Involvement of endogenous Orphanin FQ in electroacupuncture-induced analgesia." *NeuroReport*, 1997, 8:497).

A growing body of evidence supports a more generalized regulatory role for ORL-1 against the actions of the μ receptor, possibly contributing to the development of μ-agonist tolerance in patients being treated with classical opiates (e.g., J. Tian et al., "Functional studies using antibodies against orphanin FQ/nociceptin." *Peptides*, 2000, 21:1047; and H. Ueda et al., "Enhanced Spinal Nociceptin Receptor Expression Develops Morphine Tolerance and Dependence." *J. Neurosci.*, 2000, 20:7640). Moreover, ORL-1 activation appears to have an inhibitory effect on the rewarding properties of several drugs of abuse, including μ agonists.

Certain compounds have been described as at least partial agonists for ORL-1 (e.g., buprenorphine ($IC_{50}$ of 8.4 nM), fentanyl ($IC_{50}$ of about 10,000 nM), 7-benzylidenenaltrexone ($IC_{50}$ about 10,000 nM) (S. Wnendt et al., "Agonistic effect of buprenorphine in a nociceptin/OFQ receptor-triggered reporter gene assay." *Molec. Pharmacol.*, 1999, 56:334-338), and etorphine ($IC_{50}$ of about 2000 nM) (Hawkinson et al., "Opioid activity profiles indicate similarities between the nociceptin/orphanin FQ and opioid receptors." *Eur. J. Pharmacol*, 2000, 389:107-114)). However, buprenorphine's μ potency is disclosed to be much greater than its ORL-1 potency.

Recent data have shown that the analgesic efficacy of buprenorphine is enhanced by pre-treatment with an ORL-1 receptor antagonist. Using the tail-flick test in mice, Lutfy et al. demonstrated that buprenorphine's typical bell-shaped dose-response curve (wherein low and high doses induce little analgesia, and mid-range doses produce maximal analgesia) is eliminated by pre-treatment with the ORL-1 antagonist J-113397, and analgesic efficacy is improved at the higher range of doses (K. Lutfy et al., "Buprenorphine-induced antinociception is mediated by μ-opioid receptors and compromised by concomitant activation of opioid receptor-like receptors." *J. Neurosci.*, 2003, 23:10331-10337).

Recently, a multidisciplinary group of experts in the fields of pharmacology, toxicology, pain management, and anesthesia have recommended buprenorphine as the best opioid for treating chronic severe pain in elderly patients (Pergolizzi, et al. (2008). Opioids and the Management of Chronic Severe Pain in the Elderly: Consensus Statement of an International Expert Panel with Focus on the Six Clinically Most Often Used World Health Organization step IB Opioids (buprenorphine, Fentanyl, Hydromorphone, Methadone, Morphine, Oxycodone. *Pain Practice* 8(4): 287-313)). It was found that of the opioids studied, buprenorphine provided the best analgesic-to-side effect profile. Buprenorphine was the most effective opioid for treating neuropathic pain. Buprenorphine was the only opioid for which metabolism was not affected by impaired renal function. Buprenorphine was the only opioid demonstrating a ceiling effect for respiratory depression, indicating that higher doses may be used. Also, buprenorphine was the least likely to induce immunosuppression. The panel of experts attributed the improved therapeutic efficacy of buprenorphine to its unique pharmacological profile.

Buprenorphine has also been shown to have an improved side effect profile in animal models. A review of recent data in animal models of reward and addiction has shown that buprenorphine has a low addictive and dependence-inducing profile compared to other opioids (Tzschentike (2002). Behavioral pharmacology of buprenorphine, with a focus on preclinical models of reward and addiction. *Psychopharmacology* 161: 1-16).

Use of opioid analgesics often leads to constipation as a side effect. Constipation associated with the use of opioid analgesics is presumed to occur primarily and mechanistically as a result of the action of μ opioid agonists directly upon μ opioid receptors located in the bowel (Wood & Galligan (2004), Function of opioids in the enteric nervous system. *Neurogastroenterology & Motility* 16(Suppl. 2): 17-28.). Stimulation of the μ opioid receptors in the bowel causes inhibition of normal gastrointestinal (GI) motility, leading to constipation. The effect of μ opioid agonism on μ opioid receptors in the bowel can be observed via the action of loperamide (Imodium™) in treating diarrhea. Loperamide is a potent μ opioid agonist that is administered orally, but which has little to no absorption into the blood stream. As a result, loperamide exerts its action locally upon the μ opioid receptors in the bowel, and this results in inhibition of GI motility, which treats diarrhea.

There has been recent interest in developing combinations of μ receptor agonists and antagonists having defined biodistribution properties that might serve to limit opioid-induced constipation. For example, the co-administration of an orally bio-available μ opioid receptor agonist (such as morphine, codeine, oxycodone or hydrormorphone) together with a potent μ opioid receptor antagonist (such as N-methylnaloxone or N-methylnaltrexone) that is not orally bio-available may serve to prevent or reduce the constipation otherwise associated with μ opioid receptor agonist therapy. The rationale is that the agonist component will be absorbed and distributed throughout the periphery and the central nervous system (CNS), resulting in the desired analgesia, while the antagonist component will remain in the bowel where it will prevent or reduce any agonist-induced constipation that might otherwise occur.

There remains a need in the art to identify and develop novel buprenorphine analogs having improved therapeutic efficacy while reducing adverse side effects.

BRIEF SUMMARY OF THE INVENTION

The present invention provides novel buprenorphine analog compounds useful for treating, preventing or ameliorating a variety of conditions, including pain, in particular chronic pain, and constipation. More specifically, the present invention provides compounds of Formula I, Formula II, Formula III, Formula IV, and Formula V below, and the pharmaceutically acceptable salts, and solvates thereof, that exhibit affinity for one or more of the ORL-1, μ, δ, and/or κ opioid receptors. Such compounds, salts, and solvates are collectively referred to hereinafter as "Compounds of the Invention" (each is individually referred to hereinafter as a "Compound of the Invention").

In a particular aspect, the present invention provides novel compounds of Formula I:

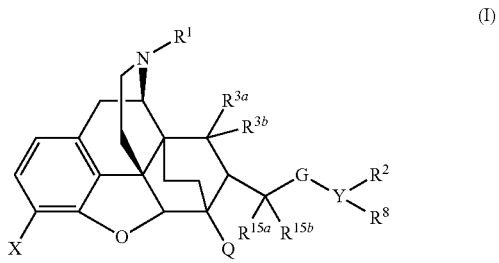

(I)

wherein
$R^1$ is selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, ($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(6- to 14-membered)aryl, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents each independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —CONR$^9$R$^{10}$, —NR$^9$COR$^{10}$, —SR$^9$, -(5- to 12-membered)carbocyclic ring, -(5- to 12-membered)heterocycle, phenyl, and benzyl;

$R^2$ and $R^8$ are each independently selected from the group consisting of hydrogen, —($C_1$-$C_{10}$)alkyl, —($C_2$-$C_{12}$)alkenyl, —($C_2$-$C_{12}$)alkynyl, —CONR$^5$R$^6$, —COOR$^7$-(6- to 14-membered)aryl, ((6- to 14-membered)aryl)-($C_1$-$C_6$)alkyl-, -(5- to 12-membered)heteroaryl, or ((5- to 12-membered)heteroaryl)-($C_1$-$C_6$)alkyl-; each of which is optionally substituted with 1, 2, or 3 substituents each independently selected from the group consisting of —OH, (═O), halo, —C(halo)$_3$, —CH(halo)$_2$, —CH$_2$(halo), —($C_1$-$C_6$) alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)-CO—($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-R$^{14}$, —CN, —SH, —OR$^4$, —CONR$^5$R$^6$, —($C_1$-$C_6$alkyl)-CO—NR$^5$R$^6$, —COOR$^7$, and —($C_1$-$C_6$)alkyl-CO—OR$^7$;

$R^{3a}$ and $R^{3b}$ are each independently selected from the group consisting of hydrogen, —($C_1$-$C_{10}$)alkyl, —($C_2$-$C_{10}$)alkenyl, —($C_2$-$C_{10}$)alkynyl, —CONR$^5$R$^6$, and —COOR$^7$, or together form (═O);

$R^4$ is selected from the group consisting of —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, -(6- to 14-membered)aryl, ((6- to 14-membered)aryl)-($C_1$-$C_6$) alkyl-, -(5- to 12-membered)heteroaryl, and ((5- to 12-membered)heteroaryl)-($C_1$-$C_6$)alkyl-;

$R^5$ and $R^6$ are each independently selected from the group consisting of hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, and ($C_1$-$C_6$)alkyl- CONH—, or $R^5$ and $R^6$ together with the nitrogen atom to which they are attached form a (4- to 8-membered)heterocycle;

$R^7$ is selected from the group consisting of hydrogen, —$(C_1-C_6)$alkyl, —$(C_2-C_6)$alkenyl, —$(C_2-C_6)$alkynyl, —$(C_3-C_{12})$cycloalkyl, —$(C_4-C_{12})$cycloalkenyl, $((C_3-C_{12})$cycloalkyl)-$(C_1-C_6)$alkyl-, and $((C_4-C_{12})$cycloalkenyl)-$(C_1-C_6)$alkyl-;

$R^9$ and $R^{10}$ are each independently selected from the group consisting of hydrogen, —$(C_1-C_6)$alkyl, —$(C_2-C_6)$alkenyl, —$(C_2-C_6)$alkynyl, —$(C_1-C_{10})$alkoxy, —$(C_3-C_{12})$cycloalkyl, —$(C_4-C_{12})$cycloalkenyl, $((C_3-C_{12})$cycloalkyl)-$(C_1-C_6)$alkyl-, and $((C_4-C_{12})$cycloalkenyl)-$(C_1-C_6)$alkyl-;

$R^{12}$ and $R^{13}$ are each independently selected from the group consisting of hydrogen, —$(C_1-C_{10})$alkyl, —$(C_2-C_{12})$alkenyl, —$(C_2-C_{12})$alkynyl, —$(C_1-C_{10})$alkoxy, —$(OCH_2CH_2)_s$—$O(C_1-C_6)$alkyl, —$(C_3-C_{12})$cycloalkyl, $((C_3-C_{12})$cycloalkyl)-$(C_1-C_6)$alkyl-, —$(C_4-C_{12})$cycloalkenyl, $((C_4-C_{12})$cycloalkenyl)-$(C_1-C_6)$alkyl-, —$(C_6-C_{14})$bicycloalkyl, $((C_6-C_{14})$bicycloalkyl)-$(C_1-C_6)$alkyl-, —$(C_8-C_{20})$tricycloalkyl, $((C_8-C_{20})$tricycloalkyl)-$(C_1-C_6)$alkyl-, —$(C_7-C_{14})$bicycloalkenyl, $((C_7-C_{14})$bicycloalkenyl)-$(C_1-C_6)$alkyl-, —$(C_8-C_{20})$tricycloalkenyl, $((C_8-C_{20})$tricycloalkenyl)-$(C_1-C_6)$alkyl-, -(6- to 14-membered)aryl, $((6$- to 14-membered)aryl)-$(C_1-C_6)$alkyl-, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl and naphthyl; each of which is optionally substituted with 1 or 2 substituents each independently selected from the group consisting of OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, phenyl, benzyl, NH$_2$, —NH$(C_1-C_6)$alkyl, CN, SH, OR$^4$, —CONR$^5$R$^6$, —COOR$^7$, —$(C_3-C_{12})$cycloalkyl, $((C_3-C_{12})$cycloalkyl)-$(C_1-C_6)$alkyl-, -(6- to 14-membered)aryl, ((6- to 14-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

$R^{14}$ is selected from the group consisting of —COOR$^7$, —$(C_1-C_6)$alkyl-CO—OR$^7$, —C(=O)—$(C_1-C_6)$alkyl-COOR$^7$, —$(C_1-C_6)$alkyl-C(=O)—$(C_1-C_6)$alkyl-COOR$^7$, —CONH$_2$, and $(C_1-C_6)$alkyl-CONH—;

G is selected from the group consisting of CH$_2$, NR$^{16}$, and O;

X is selected from the group consisting of —$(C_1-C_{10})$alkoxy, OH, hydroxy$(C_1-C_6)$alkyl-, dihydroxy$(C_1-C_6)$alkyl-, halogen, —NH$_2$, —NR$^2$(C=O)R$^{12}$, and —CONR$^{12}$R$^{13}$;

Q is selected from the group consisting of OH, —$(C_1-C_{10})$alkoxy, —$(C_1-C_{10})$alkyl, —O—$(C_1-C_6)$alkyl, -(6- to 14-membered)aryl, —O-((6- to 14-membered)aryl), ((6- to 14-membered)aryl)-$(C_1-C_6)$alkyl-, —O-((6- to 14-membered)aryl)-$(C_1-C_6)$alkyl, (5- to 12-membered)heteroaryl, —O-((5- to 12-membered)heteroaryl), ((5- to 12-membered)heteroaryl)-$(C_1-C_6)$alkyl-, and —O-((5- to 12-membered)heteroaryl-$(C_1-C_6)$alkyl;

$R^{15a}$ and $R^{15b}$ are each independently selected from the group consisting of:

a) hydrogen, OH;
b) saturated, unsaturated, or partially saturated —$(C_3-C_{12})$cycloalkyl, $((C_3-C_{12})$cycloalkyl)-$(C_1-C_6)$alkyl-, $((C_3-C_{12})$cycloalkyl)-$(C_2-C_6)$alkenyl-, and $((C_3-C_{12})$cycloalkyl)-$(C_1-C_6)$alkoxy-;
c) -(6- to 14-membered)aryl, ((6- to 14-membered)aryl)-$(C_1-C_6)$alkyl-, ((6- to 14-membered)aryl)-$(C_1-C_6)$alkoxy-, and ((6- to 14-membered)aryl)-$(C_2-C_6)$alkenyl-;
d) -(5- to 12-membered)heteroaryl, ((5- to 12-membered)heteroaryl)-$(C_1-C_6)$alkyl-, ((5- to 12-membered)heteroaryl)-$(C_1-C_6)$alkoxy-, and ((5- to 12-membered)heteroaryl)-$(C_2-C_6)$alkenyl-; and
e) -(3- to 12-membered)heterocycle, ((3- to 12-membered)heterocycle)-$(C_1-C_6)$alkyl-, ((3- to 12-membered)heterocycle)-$(C_1-C_6)$alkoxy-, -(7- to 12-membered)bicycloheterocycle, ((7- to 12-membered)bicycloheterocycle)-$(C_1-C_6)$alkyl-, and ((7- to 12-membered)bicycloheterocycle)-$(C_1-C_6)$alkoxy-;

provided that at least one of $R^{15a}$ and $R^{15b}$ is other than hydrogen;

$R^{16}$ is selected from the group consisting of hydrogen and —$(C_1-C_6)$alkyl;

Y is —$(CH_2)_m$—CH or a direct bond, provided that when Y is a direct bond then $R^8$ is absent;

n is an integer 0, 1, 2, 3, 4, 5 or 6;

s is an integer 1, 2, 3, 4, 5, 6, 7, 8, 9, 10, 11, 12, or 13;

and the pharmaceutically acceptable salts, or solvates thereof.

In one embodiment, the present invention provides novel compounds of Formula II:

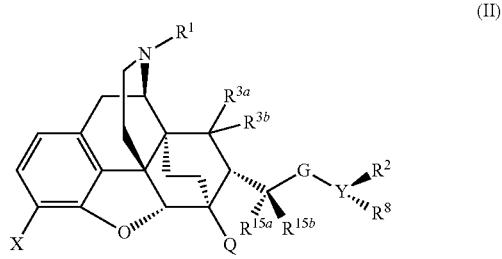

wherein $R^1$, $R^2$, $R^{3a}$, $R^{3b}$, $R^8$, $R^{15a}$, $R^{15b}$, Q and X are as defined above for Formula I.

In another embodiment, the present invention provides novel compounds of Formula III:

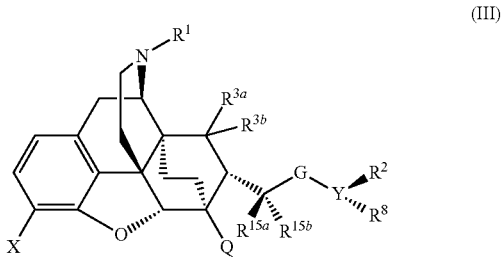

wherein $R^1$, $R^2$, $R^{3a}$, $R^{3b}$, $R^8$, $R^{15a}$, $R^{15b}$, Q and X are as defined above for Formula I.

In another embodiment, the present invention provides novel compounds of Formula IV:

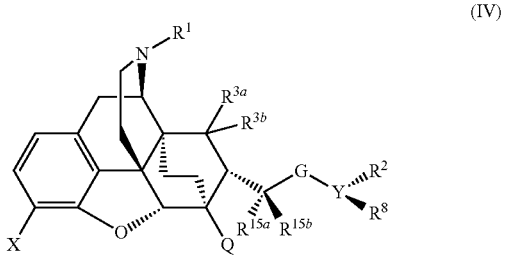

(IV)

wherein $R^1$, $R^2$, $R^{3a}$, $R^{3b}$, $R^8$, $R^{15a}$, $R^{15b}$, Q and X are as defined above for Formula I.

In another embodiment, the present invention provides novel compounds of Formula V:

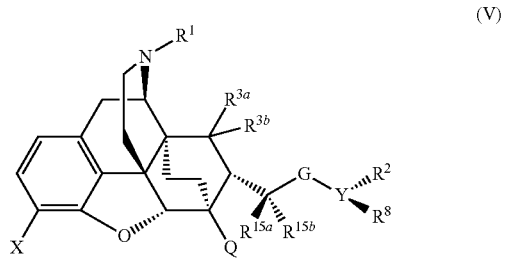

(V)

wherein $R^1$, $R^2$, $R^{3a}$, $R^{3b}$, $R^8$, $R^{15a}$, $R^{15b}$, Q and X are as defined above for Formula I.

It is an object of certain embodiments of the present invention to provide new compounds that are therapeutically effective at treating a Condition, while having reduced side effects (such as opioid-induced constipation) compared to compounds currently available.

Certain Compounds of the Invention have agonist activity at the μ, δ and/or κ receptors which is greater than currently available compounds, e.g., morphine.

Certain Compounds of the Invention have both: (i) antagonist activity at the ORL-1 receptor; and (ii) agonist activity at one or more of the μ, δ and/or κ receptors. Certain Compounds of the Invention have both: (i) antagonist activity at the ORL-1 receptor; and (ii) agonist activity at the μ receptor. Certain compounds of the invention will have both: (i) antagonist activity at the μ receptor; and (ii) agonist activity at the κ receptor. Certain compounds of the invention will have: (i) antagonist activity at the ORL-1 receptor; (ii) antagonist activity at the μ receptor; and (iii) agonist activity at the κ receptor. Certain compounds of the invention will have: (i) antagonist activity at the μ receptor; (ii) agonist activity at the κ receptor; and (iii) antagonist activity at the δ receptor.

Compounds of the Invention may be useful as analgesics to treat, ameliorate, or prevent pain; or as agents to treat, ameliorate, or prevent addictive disorders; or as agents to treat, ameliorate, or prevent withdrawal from alcohol and/or drugs of addiction; or as agents to treat, ameliorate, or prevent pruritic conditions; or as agents to treat or prevent constipation; or as agents to treat or prevent diarrhea (each of pain, alcohol withdrawal, drug withdrawal, addictive disorders, pruritis, constipation, and diarrhea being a "Condition").

In a further aspect, the present invention provides methods for treating a Condition, comprising administering to a subject in need thereof a therapeutically effective amount of a Compound of the Invention. In certain embodiments, the Condition is pain (chronic or acute pain). The Compounds of the Invention are particularly useful for treating chronic pain.

Compounds of the Invention can be used to treat, ameliorate, or prevent acute or chronic pain. Examples of pain that can be treated, ameliorated, or prevented using a Compound of the Invention include, but are not limited to, cancer pain, neuropathic pain, labor pain, myocardial infarction pain, pancreatic pain, colic pain, post-operative pain, headache pain, migraine pain, muscle pain, arthritic pain, and pain associated with a periodontal disease, including gingivitis and periodontitis.

Compounds of the Invention can also be used to treat, ameliorate, or prevent pain associated with inflammation or with an inflammatory disease in an animal. Such pain can arise where there is an inflammation of the body tissue which can be a local inflammatory response or a systemic inflammation. For example, a Compound of the Invention can be used to treat, ameliorate, or prevent pain associated with inflammatory diseases including, but not limited to, organ transplant rejection; reoxygenation injury resulting from organ transplantation (see Grupp et al., *J. Mol, Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. Compounds of the Invention can also be used to treat, ameliorate, or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Compounds of the Invention can also be used to treat, ameliorate, or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

Compounds of the Invention can be used to treat, ameliorate, or prevent pain associated with migraine including, but not limited to, migraine without aura ("common migraine"), migraine with aura ("classic migraine"), migraine without headache, basilar migraine, familial hemiplegic migraine, migrainous infarction, and migraine with prolonged aura.

Another object of the invention is to provide buprenorphine analog compounds useful for treating, ameliorating, or preventing constipation, preferably μ opioid receptor-induced constipation, by administering an effective amount of a Compound of the Invention to a patient in need of such treatment or prevention. In one embodiment, the Compound of the Invention is a μ antagonist that is substantially restricted to the GI tract. In another embodiment, the Compound of the Invention is both a μ antagonist and a κ agonist, and is substantially restricted to the GI tract. In another embodiment, the method comprises co-administering to a patient both an effective amount of a Compound of the Invention that is a μ antagonist and is substantially restricted to the GI tract, and an analgesically effective amount of a μ agonist. In another embodiment, the method comprises co-administration to a patient of both an effective amount of a Compound of the Invention that is both a μ antagonist and a κ agonist, and which is substantially restricted to the GI tract, and an analgesically effective amount of a μ agonist. Compounds of the Invention that have μ antagonist activity and are substantially restricted to the GI tract will significantly reduce or prevent constipation that would otherwise occur in a patient as a result of treatment with a μ agonist. In one embodiment, the reduction or prevention of constipation is obtained without substantially reducing the desired analgesic effect of the μ agonist. Compounds of the Invention that also exhibit κ agonist activity should additionally stimulate GI motility via a non-μ receptor-mediated mechanism.

In certain non-limiting embodiments, the Compound of the Invention exhibits a substantially linear dose response curve, such that the bell-shaped dose response curve observed for most opioid analgesics (i.e. low and high doses do not produce significant analgesia, whereas mid-range doses produce analgesia) is not observed for the Compound of the Invention. It is expected, therefore, that it will be easier to titrate to an effective dose of the Compound of the Invention in a patient than it is for conventional opioid analgesics. It is further expected that the Compound of the Invention will produce effective analgesia and/or anti-hyperalgesia in a patient who has become tolerant to conventional opioids, and for whom a conventional opioid is no longer an effective treatment. It is further expected that a Compound of the Invention will produce effective analgesia and/or anti-hyperalgesia at doses that do not induce side effects such as respiratory depression in patients for whom a dose of a conventional opioid that is high enough to be an effective treatment also induces significant side effects such as respiratory depression.

In a further aspect, the present invention provides methods for preventing a Condition, comprising administering to an subject in need thereof a Condition-preventing effective amount of a Compound of the Invention.

In a further aspect, the present invention provides pharmaceutical compositions comprising a therapeutically effective amount of a Compound of the Invention admixed with a pharmaceutically acceptable carrier or excipient. Such compositions are useful for treating, ameliorating, or preventing a Condition in a subject. The pharmaceutical compositions of the present invention may be formulated as immediate release formulations, or as controlled or sustained release formulations. Pharmaceutical compositions of the present invention may be formulated for administration by any of a number of different routes known in the art, including but not limited to, oral, intradermal, intramuscular, intraperitoneal, parenteral, intravenous, subcutaneous, intranasal, epidural, sublingual, intracerebral, intravaginal, transdermal, transmucosal, rectal, by inhalation, or topical (particularly to the ears, nose, eyes, or skin).

In a further aspect, the present invention provides methods for preparing a composition, comprising the step of admixing a Compound of the Invention and a pharmaceutically acceptable carrier or excipient to form a pharmaceutical composition.

In a further aspect, the invention still further relates to a kit comprising a sterile container containing an effective amount of a Compound of the Invention, and instructions for therapeutic use.

DETAILED DESCRIPTION OF THE INVENTION

The Compounds of the Invention are novel buprenorphine analogs. They are useful for treating, ameliorating, or preventing one or more Conditions, such as pain or constipation. Compounds of the Invention may provide a reduced liability for developing analgesic tolerance and physical dependence.

The Compounds of the Invention are useful for modulating a pharmacodynamic response from one or more opioid receptors (μ, δ, κ, or ORL-1) either centrally or peripherally, or both. The pharmacodynamic response may be attributed to the compound stimulating (agonizing) or inhibiting (antagonizing) the one or more receptors. Certain Compounds of the Invention may inhibit (or antagonize) the ORL-1 receptor, while also stimulating (or agonizing) one or more other receptors (e.g. as a μ, δ and/or κ agonist). Compounds of the Invention having agonist activity may be either full or partial agonists.

In certain embodiments, Compounds of the Invention can be used in combination with at least one other therapeutic agent. The other therapeutic agent can be, but is not limited to, a μ-opioid agonist, a non-opioid analgesic, a non-steroidal anti-inflammatory agent, a Cox-II inhibitor, an anti-emetic, a β-adrenergic blocker, an anticonvulsant, an antidepressant, a $Ca^{2+}$-channel blocker, an anticancer agent, or a mixture thereof.

Various objects and advantages of the present invention will become apparent from the following detailed description.

Item 1. The present invention provides novel compounds of Formula I:

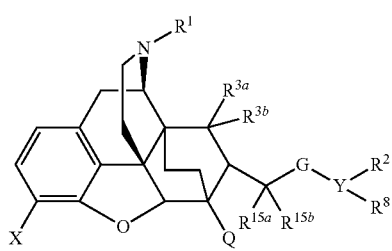

(I)

wherein $R^1$ is selected from the group consisting of hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, $((C_4$-$C_{12})$cycloalkenyl)-$(C_1$-$C_6)$alkyl-, -(6- to 14-membered)aryl, ((6- to 14-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, phenyl, and benzyl; any of which is optionally substituted with 1, 2, or 3 substituents each independently selected from the group consisting of —$(C_1$-$C_6)$alkyl, OH, halo, —C(halo)$_3$, —CH(halo)$_2$, —CH$_2$(halo), —$(C_1$-$C_6)$alkyl-COOR$^7$, —COOR$^7$, NH$_2$, —NH$(C_1$-$C_6)$alkyl, —NR$^9$R$^{10}$, —CN, —CONR$^9$R$^{10}$, —NR$^9$COR$^{10}$, —SR$^9$, -(5- to 12-membered)carbocyclic ring, -(5- to 12-membered)heterocycle, phenyl, and benzyl;

$R^2$ and $R^8$ are each independently selected from the group consisting of hydrogen, —$(C_1$-$C_{10})$alkyl, —$(C_2$-$C_{12})$alkenyl, —$(C_2$-$C_{12})$alkynyl, —CONR$^5$R$^6$, —COOR$^7$, -(6- to 14-membered)aryl, ((6- to 14-membered)aryl)-$(C_1$-$C_6)$alkyl-, -(5- to 12-membered)heteroaryl, and ((5- to 12-membered)heteroaryl)-$(C_1$-$C_6)$alkyl-; each of which is optionally substituted with 1, 2, or 3 substituents independently selected from the group consisting of —OH, (=O), halo, —C(halo)$_3$, —CH(halo)$_2$, —CH$_2$(halo), —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, dihydroxy$(C_1$-$C_6)$alkyl-, —$(C_1$-$C_6)$alkoxy, $((C_1$-$C_6)$alkoxy)-CO—$(C_1$-$C_6)$alkoxy-, phenyl, benzyl, —NH$_2$, —NH$(C_1$-$C_6)$alkyl, —$(C_1$-$C_6)$alkyl-NH$(C_1$-$C_6)$alkyl-R$^{14}$, —CN, —SH, —OR$^4$, —CONR$^5$R$^6$, —$(C_1$-$C_6$alkyl)-CO—NR$^5$R$^6$, —COOR$^7$, and —$(C_1$-$C_6)$alkyl-CO—OR$^7$;

$R^{3a}$ and $R^{3b}$ are each independently selected from the group consisting of hydrogen, —$(C_1$-$C_{10})$alkyl, —$(C_2$-$C_{10})$alkenyl, —$(C_2$-$C_{10})$alkynyl, —CONR$^5$R$^6$, —COOR$^7$, or together form (=O);

$R^4$ is selected from the group consisting of —$(C_1$-$C_6)$alkyl, —$(C_2$-$C_6)$alkenyl, —$(C_2$-$C_6)$alkynyl, —C(halo)$_3$, —CH(halo)$_2$, —CH$_2$(halo), hydroxy$(C_1$-$C_6)$alkyl-, —$(C_3$-$C_{12})$cycloalkyl, $((C_3$-$C_{12})$cycloalkyl)-$(C_1$-$C_6)$alkyl-, -(6- to 14-membered)aryl, ((6- to 14-membered)aryl)-$(C_1$-$C_6)$alkyl-, -(5- to 12-membered)heteroaryl, and ((5- to 12-membered)heteroaryl)-$(C_1$-$C_6)$alkyl-;

$R^5$ and $R^6$ are each independently selected from the group consisting of hydrogen, —$(C_1$-$C_6)$alkyl, —$(C_3$-$C_8)$cycloalkyl, $((C_3$-$C_8)$cycloalkyl)-$(C_1$-$C_6)$alkyl-, —COOR$^7$, —$(C_1$-$C_6)$alkyl-CO—OR$^7$, —CONH$_2$, and $(C_1$-$C_6)$alkyl-CONH—, or $R^5$ and $R^6$ together with the nitrogen atom to which they are attached form a (4- to 8-membered)heterocycle;

$R^7$ is selected from the group consisting of hydrogen, —$(C_1$-$C_6)$alkyl, —$(C_2$-$C_6)$alkenyl, —$(C_2$-$C_6)$alkynyl, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, and $((C_4$-$C_{12})$cycloalkenyl)-$(C_1$-$C_6)$alkyl-;

$R^9$ and $R^{10}$ are each independently selected from the group consisting of hydrogen, —$(C_1$-$C_6)$alkyl, —$(C_2$-$C_6)$alkenyl, —$(C_2$-$C_6)$alkynyl, —$(C_1$-$C_{10})$alkoxy, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, and $((C_4$-$C_{12})$cycloalkenyl)-$(C_1$-$C_6)$alkyl-;

$R^{12}$ and $R^{13}$ are each independently selected from the group consisting of hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —(OCH$_2$CH$_2$)$_s$—O$(C_1$-$C_6)$alkyl, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(6- to 14-membered)aryl, ((6- to 14-membered)aryl)-$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl and naphthyl; each of which is optionally substituted with 1 or 2 substituents independently selected from the group consisting of OH, (=O), halo, —C(halo)$_3$, —CH(halo)$_2$, —CH$_2$(halo), —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, phenyl, benzyl, NH$_2$, —NH$(C_1$-$C_6)$alkyl, CN, SH, OR$^4$, —CONR$^5$R$^6$, —COOR$^7$, —$(C_3$-$C_{12})$cycloalkyl, $((C_3$-$C_{12})$cycloalkyl)-$(C_1$-$C_6)$alkyl-, -(6- to 14-membered)aryl, ((6- to 14-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^{14}$ is selected from the group consisting of —COOR$^7$, —$(C_1$-$C_6)$alkyl-CO—OR$^7$, —C(=O)—$(C_1$-$C_6)$alkyl-COOR$^7$, —$(C_1$-$C_6)$alkyl-C(=O)—$(C_1$-$C_6)$alkyl-COOR$^7$, —CONH$_2$, and $(C_1$-$C_6)$alkyl-CONH—;

G is selected from the group consisting of CH$_2$, NR$^{16}$, or O;

X is selected from the group consisting of —$(C_1$-$C_{10})$alkoxy, OH, hydroxy$(C_1$-$C_6)$alkyl-, dihydroxy$(C_1$-$C_6)$alkyl-, halogen, —NH$_2$, —NR$^2(C=O)R^{12}$, and —CONR$^{12}$R$^{13}$;

Q is selected from the group consisting of OH, —$(C_1$-$C_{10})$alkoxy, —$(C_1$-$C_{10})$alkyl, —O—$(C_1$-$C_6)$alkyl, -(6- to 14-membered)aryl, —O-((6- to 14-membered)aryl), ((6- to 14-membered)aryl)-$(C_1$-$C_6)$alkyl-, —O-(6- to 14-membered)aryl)-$(C_1$-$C_6)$alkyl, (5- to 12-membered)heteroaryl, —O-((5- to 12-membered)heteroaryl), ((5- to 12-membered)heteroaryl)-($C_1$-$C_6$)alkyl-, —O-((5- to 12-membered)heteroaryl-($C_1$-$C_6$)alkyl;

$R^{15a}$ and $R^{15b}$ are each independently selected from the group consisting of:
a) hydrogen, OH;
b) saturated, unsaturated, or partially saturated —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_2$-$C_6$)alkenyl-, (($C_3$-$C_{12}$)cycloalkyl)-($C_1$-$C_6$)alkoxy-;
c) -(6- to 14-membered)aryl, ((6- to 14-membered)aryl)-($C_1$-$C_6$)alkyl-, ((6- to 14-membered)aryl)-($C_1$-$C_6$)alkoxy-, ((6- to 14-membered)aryl)-($C_2$-$C_6$)alkenyl-;
d) -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_2$-$C_6$)alkenyl-; and
e) -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-.
provided that at least one of $R^{15a}$ and $R^{15b}$ is other than hydrogen;

$R^{16}$ is selected from the group consisting of hydrogen or —($C_1$-$C_6$)alkyl;

Y is —($CH_2$)$_n$—CH or a direct bond, provided that when Y is a direct bond then $R^8$ is absent;

n is an integer 0, 1, 2, 3, 4, 5 or 6;

s is an integer 1, 2, 3, 4, 5, 6, 7, 8, 9, 10, 11, 12, or 13;

and the pharmaceutically acceptable salts, or solvates thereof.

Item 2. In one embodiment of Item 1, the present invention provides novel compounds of Formula II:

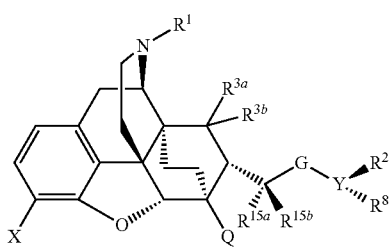

(II)

wherein $R^1$, $R^2$, $R^{3a}$, $R^{3b}$, $R^8$, $R^{15a}$, $R^{15b}$, Q and X are as defined above for Formula I.

Item 3. In another embodiment Item 1, the present invention provides novel compounds of Formula III:

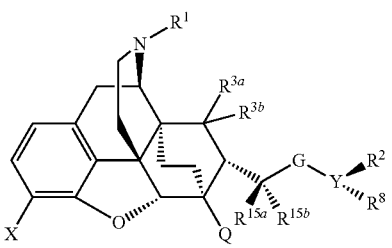

(III)

wherein $R^1$, $R^2$, $R^{3a}$, $R^{3b}$, $R^8$, $R^{15a}$, $R^{15b}$, Q and X are as defined above for Formula I.

Item 4. In another embodiment of Item 1, the present invention provides novel compounds of Formula IV:

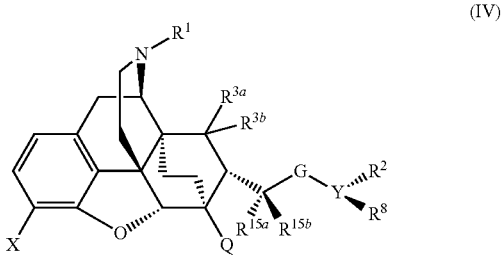

(IV)

wherein $R^1$, $R^2$, $R^{3a}$, $R^{3b}$, $R^8$, $R^{15a}$, $R^{15b}$, Q and X are as defined above for Formula I.

Item 5. In another embodiment of Item 1, the present invention provides novel compounds of Formula V:

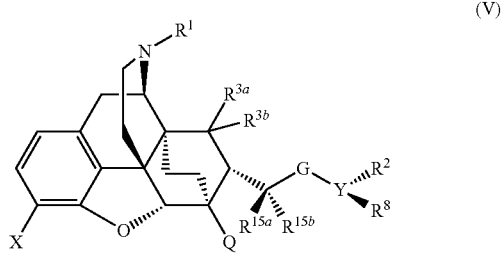

(V)

wherein $R^1$, $R^2$, $R^{3a}$, $R^{3b}$, $R^8$, $R^{15a}$, $R^{15b}$, Q and X are as defined above for Formula I.

Item 6. In one embodiment of any one of Items 1 to 5, G is $NR^{16}$.

Item 7. In one embodiment of Item 6, G is $NR^{16}$, wherein $R^{16}$ is hydrogen.

Item 8. In another embodiment of any one of Items 1 to 5, G is $CH_2$.

Item 9. In another embodiment of any one of Items 1 to 5, G is O.

Item 10. In one embodiment of any one of Items 1 to 9, at least one of $R^{15a}$ or $R^{15b}$ is -(6- to 14-membered)aryl.

Item 11. In one embodiment of Item 10, at least one of $R^{15a}$ or $R^{15b}$ is phenyl.

Item 12. In another embodiment of any one of Items 1 to 9, at least one of $R^{15a}$ or $R^{15b}$ is (6- to 14-membered)aryl-($C_1$-$C_6$)alkyl-.

Item 13. In one embodiment of Item 12, at least one of $R^{15a}$ or $R^{15b}$ is benzyl.

Item 14. In another embodiments of any one of Items 1 to 9, at least one of $R^{15a}$ or $R^{15b}$ is hydrogen.

Item 15. In another embodiment of any one of Items 1 to 9, at least one of $R^{15a}$ or $R^{15b}$ is OH.

Item 16. In one embodiment of any one of Items 1 to 9, at least one of $R^2$ or $R^8$ is —($C_1$-$C_{10}$)alkyl.

Item 17. In another embodiment of any one of Items 1 to 9 or 16, at least one of $R^2$ or $R^8$ is —($C_1$-$C_{10}$)alkyl substituted with —$COOR^7$.

Item 18. In certain embodiments of Item 17, $R^7$ is hydrogen.

Item 19. In another embodiment of any one of Items 1 to 9 or 16, at least one of $R^2$ or $R^8$ is —($C_1$-$C_{10}$)alkyl substituted with —$CONR^5R^6$.

Item 20. In certain embodiments of Item 19, $R^5$ and $R^6$ are both hydrogen.

Item 21. In another embodiment of any one of Items 1 to 9, at least one of $R^2$ or $R^8$ is -(6- to 14-membered)aryl.

Item 22. In one embodiment of Item 21, at least one of $R^2$ or $R^8$ is phenyl.

Item 23. In another embodiment, at least one of $R^2$ or $R^8$ is (6- to 14-membered)aryl-($C_1$-$C_6$)alkyl-.

Item 24. In one embodiment of Item 23, at least one of $R^2$ or $R^8$ is benzyl.

Item 25. In another embodiment of any one of Items 1 to 9, at least one of $R^2$ or $R^8$ is $COOR^7$.

Item 26. In certain embodiments of Item 25, $R^2$ is $COOR^7$ and $R^8$ is -(6- to 14-membered)aryl.

Item 27. In certain embodiments of any one of Items 1 to 26, $R^1$ is cyclopropylmethyl.

Item 28. In one embodiment of any one of Items 1 to 27, X is selected from the group consisting of —($C_1$-$C_{10}$)alkoxy, OH, hydroxy($C_1$-$C_6$)alkyl-, dihydroxy($C_1$-$C_6$)alkyl-, halogen, —$NH_2$, and —$NR^2(C=O)R^{12}$.

Item 29. In certain embodiments of any one of Items 1 to 28, X is —($C_1$-$C_{10}$)alkoxy.

Item 30. In one embodiment of Item 29, X is methoxy.

Item 31. In another embodiment of Item 29, X is ethoxy.

Item 32. In another embodiment of any one of Items 1 to 28, X is OH.

Item 33. In one embodiment of any one of Items 1 to 28, X is halogen.

Item 34. In certain embodiments of any one of Items 1 to 33, Q is —($C_1$-$C_{10}$)alkoxy.

Item 35. In one embodiment of Item 34, Q is methoxy.

Item 36. In another embodiment of Item 34, Q is ethoxy.

Item 37. In another embodiment of any one of Items 1 to 33, Q is OH.

Item 38. In certain embodiments of any one of Items 1 to 37, Y is CH. Item 39. In certain embodiments of any one of Items 1 to 5, Y is CH, $R^8$ is - (6- to 14-membered)aryl, and $R^2$ is $COOR^7$.

Item 40. In certain embodiments of any one of Items 1 to 5, Y is CH, $R^8$ is (6- to 14-membered)aryl-($C_1$-$C_6$)alkyl-, and $R^2$ is $COOR^7$.

Item 41. In certain embodiments of any one of Items 1 to 5, Y is CH, $R^8$ is - (6- to 14-membered)aryl, and $R^2$ is —($C_1$-$C_{10}$)alkyl substituted with —$CONR^5R^6$.

Item 42 In certain embodiments of any one of Items 1 to 5, Y is CH, $R^8$ is (6- to 14-membered)aryl-($C_1$-$C_6$)alkyl-, and $R^2$ is —($C_1$-$C_{10}$)alkyl substituted with —$CONR^5R^6$.

Item 43. In one embodiment of any one of Items 1 to 5, at least one of $R^2$ or $R^8$ is -(6- to 14-membered)aryl, and at least one of $R^{15a}$ or $R^{15b}$ is -(6- to 14-membered)aryl.

Item 44. In one embodiment of any one of Items 1 to 5, at least one of $R^2$ or $R^8$ is (6- to 14-membered)aryl-($C_1$-$C_6$)alkyl-, and at least one of $R^{15a}$ or $R^{15b}$ is -(6- to 14-membered)aryl.

Item 45. In one embodiment of any one of Items 1 to 5, at least one of $R^2$ or $R^8$ is -(6- to 14-membered)aryl, and at least one of $R^{15a}$ or $R^{15b}$ is (6- to 14-membered)aryl-($C_1$-$C_6$)alkyl-.

Item 46. In one embodiment of any one of Items 1 to 5, at least one of $R^2$ or $R^8$ is (6- to 14-membered)aryl-($C_1$-$C_6$)alkyl-, and at least one of $R^{15a}$ or $R^{15b}$ is (6- to 14-membered)aryl-($C_1$-$C_6$)alkyl-.

Compounds of the invention include:

(4R)-4-((4 R,4 aS,6 R,7 R,7 aR,12 bS)-3-(cyclopropylmethyl)-7,9-dimethoxy-1,2,3,4,5,6,7,7 a-octahydro-4 a,7-ethano-4,12-methanobenzofuro[3,2-e]isoquinolin-6-yl)-4-phenylbutane-1,2,4-triol (Compound 6);

2-(((S)-((4 R,4 aS,6 R,7 R,7 aR,12 bS)-3-(cyclopropylmethyl)-7,9-dimethoxy-1,2,3,4,5,6,7,7 a-octahydro-4 a,7-ethano-4,12-methanobenzofuro[3,2-e]isoquinolin-6-yl)(phenyl)methyl)amino)acetic acid (Compound 12);

2-(((S)-((4 R,4 aS,6 R,7 R,7 aR,12 bS)-3-(cyclopropylmethyl)-7,9-dimethoxy-1,2,3,4,5,6,7,7 a-octahydro-4 a,7-ethano-4,12-methanobenzofuro[3,2-e]isoquinolin-6-yl)(phenyl)methyl)amino)propanoic acid (Compound 13);

2-(((S)-((4 R,4 aS,6 R,7 R,7 aR,12 bS)-3-(cyclopropylmethyl)-7,9-dimethoxy-1,2,3,4,5,6,7,7 a-octahydro-4 a,7-ethano-4,12-methanobenzofuro[3,2-e]isoquinolin-6-yl)(phenyl)methyl)amino)-2-phenylacetic acid (Compound 15);

2-(((S)-((4 R,4 aS,6 R,7 R,7 aR,12 bS)-3-(cyclopropylmethyl)-7,9-dimethoxy-1,2,3,4,5,6,7,7 a-octahydro-4 a,7-ethano-4,12-methanobenzofuro[3,2-e]isoquinolin-6-yl)(phenyl)methyl)amino)propanamide (Compound 14);

(R)-2-(((S)-((4 R,4 aS,6 R,7 R,7 aR,12 bS)-3-(cyclopropylmethyl)-7,9-dimethoxy-1,2,3,4,5,6,7,7 a-octahydro-4 a,7-ethano-4,12-methanobenzofuro[3,2-e]isoquinolin-6-yl)(phenyl)methyl)amino)-2-phenylacetamide (Compound 16); and (S)-2-(((S)-((4 R,4 aS,6 R,7 R,7 aR,12 bS)-3-(cyclopropylmethyl)-7,9-dimethoxy-1,2,3,4,5,6,7,7 a-octahydro-4 a,7-ethano-4,12-methanobenzofuro[3,2-e]isoquinolin-6-yl)(phenyl)methyl)amino)-2-phenylacetamide (Compound 17).

In one embodiment, G is $NR^{16}$.

In another embodiment, G is $NR^{16}$, wherein $R^{16}$ is hydrogen.

In another embodiment, G is $CH_2$.

In another embodiment, G is O.

In one embodiment, at least one of $R^{15a}$ or $R^{15b}$ is -(6- to 14-membered)aryl.

In another embodiment, at least one of $R^{15a}$ or $R^{15b}$ is phenyl.

In another embodiment, at least one of $R^{15a}$ or $R^{15b}$ is (6- to 14-membered)aryl-($C_1$-$C_6$)alkyl-.

In another embodiment, at least one of $R^{15a}$ or $R^{15b}$ is benzyl.

In another embodiments, at least one of $R^{15a}$ or $R^{15b}$ is hydrogen.

In another embodiments, at least one of $R^{15a}$ or $R^{15b}$ is OH.

In one embodiment, at least one of $R^2$ or $R^8$ is —($C_1$-$C_{10}$)alkyl.

In another embodiment, at least one of $R^2$ or $R^8$ is —($C_1$-$C_{10}$)alkyl substituted with —$COOR^7$. In certain embodiments, $R^7$ is hydrogen.

In another embodiment, at least one of $R^2$ or $R^8$ is —($C_1$-$C_{10}$)alkyl substituted with —$CONR^5R^6$. In certain embodiments, $R^5$ and $R^6$ are both hydrogen.

In another embodiment, at least one of $R^2$ or $R^8$ is -(6- to 14-membered)aryl.

In another embodiment, at least one of $R^2$ or $R^8$ is phenyl.

In another embodiment, at least one of $R^2$ or $R^8$ is (6- to 14-membered)aryl-($C_1$-$C_6$)alkyl-.

In another embodiment, at least one of $R^2$ or $R^8$ is benzyl.

In another embodiment, at least one of $R^2$ or $R^8$ is $COOR^7$.

In certain embodiments, $R^2$ is $COOR^7$ and $R^8$ is -(6- to 14-membered)aryl.

In certain embodiments, $R^1$ is cyclopropylmethyl.

In certain embodiments, X is —($C_1$-$C_{10}$)alkoxy.

In another embodiment, X is methoxy.

In another embodiment, X is ethoxy.

In another embodiment, X is OH.

In certain embodiments, Q is —($C_1$-$C_{10}$)alkoxy.

In another embodiment, Q is methoxy.

In another embodiment, Q is ethoxy.

In another embodiment, Q is OH.

In certain embodiments, Y is CH.

In certain embodiments, Y is CH, $R^8$ is -(6- to 14-membered)aryl, and $R^2$ is $COOR^7$.

In certain embodiments, Y is CH, $R^8$ is (6- to 14-membered)aryl-$(C_1$-$C_6)$alkyl-, and $R^2$ is $COOR^7$.

In certain embodiments, Y is CH, $R^8$ is -(6- to 14-membered)aryl, and $R^2$ is —$(C_1$-$C_{10})$alkyl substituted with —$CONR^5R^6$.

In certain embodiments, Y is CH, $R^8$ is (6- to 14-membered)aryl-$(C_1$-$C_6)$alkyl-, and $R^2$ is —$(C_1$-$C_{10})$alkyl substituted with —$CONR^5R^6$.

In another embodiment, at least one of $R^2$ or $R^8$ is -(6- to 14-membered)aryl, and at least one of $R^{15a}$ or $R^{15b}$ is -(6- to 14-membered)aryl.

In another embodiment, at least one of $R^2$ or $R^8$ is (6- to 14-membered)aryl-$(C_1$-$C_6)$alkyl-, and at least one of $R^{15a}$ or $R^{15b}$ is -(6- to 14-membered)aryl.

In another embodiment, at least one of $R^2$ or $R^8$ is -(6- to 14-membered)aryl, and at least one of $R^{15a}$ or $R^{15b}$ is (6- to 14-membered)aryl-$(C_1$-$C_6)$alkyl-.

In another embodiment, at least one of $R^2$ or $R^8$ is (6- to 14-membered)aryl-$(C_1$-$C_6)$alkyl-, and at least one of $R^{15a}$ or $R^{15b}$ is (6- to 14-membered)aryl-$(C_1$-$C_6)$alkyl-.

As used herein, the term "—$(C_1$-$C_{10})$alkyl" refers to straight-chain and branched non-cyclic saturated hydrocarbons having from 1 to 10 carbon atoms. Representative straight chain —$(C_1$-$C_{10})$ alkyl groups include methyl, -ethyl, -n-propyl, -n-butyl, -n-pentyl, -n-hexyl, n-heptyl, n-octyl, n-nonyl and n-decyl. Representative branched —$(C_1$-$C_{10})$ alkyl groups include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 5-methylhexyl, 6-methylheptyl, and the like.

As used herein, the term "—$(C_1$-$C_6)$alkyl" refers to straight-chain and branched non-cyclic saturated hydrocarbons having from 1 to 6 carbon atoms. Representative straight chain —$(C_1$-$C_6)$alkyl groups include methyl, -ethyl, -n-propyl, -n-butyl, -n-pentyl, and -n-hexyl. Representative branched-chain —$(C_1$-$C_6)$alkyl groups include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl, methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, and the like.

As used herein, the term "—$(C_2$-$C_{12})$alkenyl" refers to straight chain and branched non-cyclic hydrocarbons having from 2 to 12 carbon atoms and including at least one carbon-carbon double bond. Representative straight chain and branched —$(C_2$-$C_{12})$alkenyl groups include -vinyl, allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, 3-hexenyl, and the like.

As used herein, the term "—$(C_2$-$C_6)$alkenyl" refers to straight chain and branched non-cyclic hydrocarbons having from 2 to 6 carbon atoms and including at least one carbon-carbon double bond. Representative straight chain and branched —$(C_2$-$C_6)$alkenyl groups include -vinyl, allyl, -1-butenyl, -2-butenyl, -isobutylenyl, -1-pentenyl, -2-pentenyl, -3-methyl-1-butenyl, -2-methyl-2-butenyl, 1-hexenyl, 2-hexenyl, 3-hexenyl and the like.

As used herein, the term "—$(C_2$-$C_{12})$alkynyl" refers to straight chain and branched non-cyclic hydrocarbons having from 2 to 12 carbon atoms and including at least one carbon-carbon triple bond. Representative straight chain and branched —$(C_2$-$C_{12})$alkynyl groups include -ethynyl, -propynyl, -1 butynyl, -2-butynyl, -1-pentynyl, -2-pentynyl, -3-methyl-1-butynyl, -4-pentynyl, -1-hexynyl, -2-hexynyl, -5-hexynyl, and the like.

As used herein, the term "—$(C_2$-$C_6)$alkynyl" refers to straight chain and branched non-cyclic hydrocarbons having from 2 to 6 carbon atoms and including at least one carbon-carbon triple bond. Representative straight chain and branched —$(C_2$-$C_6)$alkynyl groups include -ethynyl, -propynyl, -1 butynyl, -2-butynyl, -1-pentynyl, -2-pentynyl, -3-methyl-1-butynyl, -4-pentynyl, and the like.

As used herein, "—$(C_1$-$C_{10})$alkoxy" means a straight chain or branched non-cyclic hydrocarbon having one or more ether groups and from 1 to 10 carbon atoms. Representative straight chain and branched $(C_1$-$C_{10})$alkoxys include -methoxy, -ethoxy, -propoxy, -butyloxy, -pentyloxy, -hexyloxy, -heptyloxy, -methoxymethyl, -2-methoxyethyl, -5-methoxypentyl, -3-ethoxybutyl and the like.

As used herein, "—$(C_1$-$C_6)$alkoxy" means a straight chain or branched non-cyclic hydrocarbon having one or more ether groups and from 1 to 6 carbon atoms. Representative straight chain and branched $(C_1$-$C_6)$alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like.

As used herein, "—$(C_1$-$C_5)$alkoxy" means a straight chain or branched non-cyclic hydrocarbon having one or more ether groups and from 1 to 5 carbon atoms. Representative straight chain and branched $(C_1$-$C_5)$alkoxys include -methoxy, -ethoxy, -propoxy, -butyloxy, -pentyloxy, -methoxymethyl, -2-methoxyethyl, -5-methoxypentyl, -3-ethoxybutyl and the like.

As used herein, the term "—$(C_3$-$C_{12})$cycloalkyl" refers to cyclic saturated hydrocarbon having from 3 to 12 carbon atoms. Representative $(C_3$-$C_{12})$cycloalkyls include cyclopropyl, cyclobutyl, cyclopentyl, cyclohexyl, cycloheptyl, cyclooctyl, and cyclononyl, cyclodecyl, cycloundecyl, cyclododecyl, and the like.

As used herein, "—$(C_6$-$C_{14})$bicycloalkyl" means a bicyclic hydrocarbon ring system having from 6 to 14 carbon atoms and at least one saturated cyclic alkyl ring. Representative —$(C_6$-$C_{14})$bicycloalkyls include -indanyl, -norbornyl, -1,2,3,4-tetrahydronaphthalenyl, -5,6,7,8-tetrahydronaphthalenyl, -perhydronaphthalenyl, and the like.

As used herein, "—$(C_8$-$C_{20})$tricycloalkyl" means a tricyclic hydrocarbon ring system having from 8 to 20 carbon atoms and at least one saturated cyclic alkyl ring. Representative —$(C_8$-$C_{20})$tricycloalkyls include -pyrenyl, -adamantyl, -1,2,3,4-tetrahydroanthracenyl, -perhydroanthracenyl -aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]azulenyl, hexadecahydrocycloocta[b]naphthalenyl, hexadecahydrocyclohepta[a]heptalenyl, tricyclo-pentadecanyl, tricyclo-octadecanyl, tricyclo-nonadecanyl, tricyclo-icosanyl, and the like.

As used herein, the term "—$(C_4$-$C_{12})$cycloalkenyl" refers to a cyclic, preferably mono- or bicyclic, hydrocarbon having from 4 to 12 carbon atoms, and including at least one carbon-carbon double bond. Representative —$(C_3$-$C_{12})$cycloalkenyls include -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, and the like.

As used herein, "—($C_7$-$C_{14}$)bicycloalkenyl" means a bicyclic hydrocarbon ring system having at least one carbon-carbon double bond in at least one of the rings and from 7 to 14 carbon atoms. Representative —($C_7$-$C_{14}$)bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, and the like.

As used herein, "—($C_8$-$C_{20}$)tricycloalkenyl" means a tricyclic hydrocarbon ring system having at least one carbon-carbon double bond in one of the rings and from 8 to 20 carbon atoms. Representative —($C_8$-$C_{20}$)tricycloalkenyls include -anthracenyl, -phenanthrenyl, -phenalenyl, -acenaphthalenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta[a,c]cyclooctenyl, 2,3,4,5,6,7,8,9,10,11,12,13-dodecahydro-1H-dibenzo[a,d]cyclononenyl, and the like.

As used herein, "-(3- to 12-membered)heterocycle" or "-(3- to 12-membered)heterocyclo" means a 3- to 12-membered monocyclic heterocyclic ring which is either saturated, partially unsaturated, or non-aromatic. A 3-membered heterocycle can contain up to 1 heteroatom; a 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(3- to 12-membered)heterocycle can be attached via a nitrogen or carbon atom. Representative -(3- to 12-membered)heterocycles include thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(4- to 8-membered)heterocycle" or "-(4- to 8-membered)heterocyclo" means a 4- to 8-membered monocyclic heterocyclic ring which is either saturated, partially unsaturated, or non-aromatic. A 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(4- to 8-membered)heterocycle can be attached via a nitrogen or carbon atom. Representative -(4- to 8-membered)heterocycles include morpholinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(5- to 12-membered)heterocycle" or "-(5- to 12-membered)heterocyclo" means a 5- to 12-membered monocyclic or bicyclic heterocyclic ring which is either saturated, partially unsaturated, or non-aromatic. A 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(5- to 12-membered)heterocycle can be attached via a nitrogen or carbon atom. Representative -(5- to 12-membered)heterocycles include morpholinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(7- to 12-membered)bicycloheterocycle" or "-(7- to 12-membered)bicycloheterocyclo" means a 7- to 12-membered bicyclic, heterocyclic ring which is either saturated, partially unsaturated, ornon-aromatic. At least one ring of the bicycloheterocycle contains at least one heteroatom. A -(7- to 12-membered)bicycloheterocycle contains from 1 to 4 heteroatoms independently selected from nitrogen (which can be quaternized), oxygen, and sulfur (including sulfoxide and sulfone). The -(7- to 12-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, -indolinyl, isoindolinyl, -1,2,3,4-tetrahydroquinolinyl, -1,2,3,4-tetrahydroisoquinolinyl, pyrrolopyrrolyl and the like.

As used herein a "-(6- to 14-membered)aryl" means an aromatic carbocyclic ring containing 6 to 14 carbon atoms, including both mono-, bi-, and tricyclic ring systems. Representative -(6- to 14-membered)aryl groups include -indenyl, -phenyl, -naphthyl, anthracenyl and the like.

As used herein a "-(7- to 12-membered)bicyclic aryl" means a bicyclic aromatic carbocyclic ring containing 7 to 12 carbon atoms. Representative -(7- to 12-membered) bicyclic aryl groups include -indenyl, -naphthyl, and the like.

As used herein a "-(6- to 14-membered)aryloxy" means an oxygen substituted by an aromatic carbocyclic ring containing 6 to 14 carbon atoms, including both mono-, bi- and tricyclic ring systems. Representative -(6- to 14-membered) aryloxy groups include phenoxy and 4-fluorophenoxy, and the like.

As used herein a "hydroxy($C_1$-$C_6$)alkyl" means any of the above-mentioned $C_{1-6}$ alkyl groups substituted by one or more hydroxy groups. Representative hydroxy($C_1$-$C_6$)alkyl groups include hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

As used herein a "dihydroxy($C_1$-$C_6$)alkyl" means any of the above-mentioned $C_{1-6}$ alkyl groups substituted by two hydroxy groups. Representative dihydroxy($C_1$-$C_6$)alkyl groups include dihydroxyethyl, dihydroxypropyl and dihydroxybutyl groups, and especially 1,2-dihydroxyethyl, 1,3-dihydroxypropyl, 2,3-dihydroxypropyl, 1,3-dihydroxybutyl, 1,4-dihydroxybutyl, and 1,3-dihydroxyprop-2-yl.

As used herein a "-(5- to 12-membered)carbocyclic ring" means a mono- or bicyclic hydrocarbon ring system having from 5 to 12 carbon atoms, which is either saturated, unsaturated, or non-aromatic.

As used herein a "-(7- to 12-membered)bicyclic ring system" means a 7- to 12-membered a carbocyclic or heterocyclic ring, which may be either unsaturated, saturated, non-aromatic or aromatic.

As used herein, "-(5- to 12-membered)heteroaryl" means an aromatic heterocycle ring of 5 to 12 members, including both mono- and bicyclic ring systems, where at least one carbon atom (of one or both of the rings) is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the bicyclic -(5- to 12-membered)heteroaryl rings contains at least one carbon atom. In another embodiment, both of the bicyclic -(5- to 12-membered)heteroaryl rings contain at least one carbon atom. Representative -(5- to 12-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, thiadiazolyl, cinnolinyl, phthalazinyl, quinazolinyl, and the like.

As used herein, the terms "halo" and "halogen" refer to fluoro, chloro, bromo or iodo.

As used herein, "—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

As used herein, "—CH(halo)$_2$" means a methyl group where two of the hydrogens of the methyl group have been replaced with a halogen. Representative —CH(halo)$_2$ groups include —CHF, —$CHCl_2$, —$CHBr_2$, —CHBrCl, —CHClI, and —$CHI_2$.

As used herein, "—C(halo)$_3$" means a methyl group where each of the hydrogens of the methyl group has been replaced with a halogen. Representative —C(halo)$_3$ groups include —$CF_3$, —$CCl_3$, —$CBr_3$, and —$CI_3$.

As used herein, the term "optionally substituted" refers to a group that is either unsubstituted or substituted.

Optional substituents on optionally substituted groups, when not otherwise indicated, include 1, 2, or 3 groups each independently selected from the group consisting of —($C_1$-$C_6$)alkyl, OH, halo, —C(halo)$_3$, —CH(halo)$_2$, —$CH_2$(halo), $NH_2$, —NH($C_1$-$C_6$)alkyl, CN, SH, -(5- to 12-membered)carbocyclic ring, -(5- to 12-membered)heterocycle, phenyl, benzyl, (=O), halo($C_1$-$C_6$)alkyl-, —($C_2$-$C_6$)alkenyl, —($C_2$-$C_6$)alkynyl, hydroxy($C_1$-$C_6$)alkyl-, OR$^4$ (such as —OC(halo)$_3$ and —O($C_1$-$C_6$)alkyl), —CONR$^5$R$^6$, and —COOR$^7$, where R$^4$ is selected from the group consisting of —($C_1$-$C_6$)alkyl, —($C_2$-$C_6$)alkenyl, —($C_2$-$C_6$)alkynyl, —C(halo)$_3$, hydroxy ($C_1$-$C_6$)alkyl-, —($C_3$-$C_{12}$)cycloalkyl, —($C_6$-$C_{14}$)bicycloalkyl, —($C_8$-$C_{20}$)tricycloalkyl, —($C_4$-$C_{12}$)cycloalkenyl, —($C_7$-$C_{14}$)bicycloalkenyl, —($C_8$-$C_{20}$)tricycloalkenyl, -(6- to 14-membered)aryl, -(5- to 12-membered)heteroaryl, -(3- to 12-membered)heterocycle, and -(7- to 12-membered)bicycloheterocycle; R$^5$ and R$^6$ are each independently selected from the group consisting of —($C_1$-$C_6$)alkyl, —($C_3$-$C_8$)cycloalkyl, (($C_3$-$C_8$)cycloalkyl)-($C_1$-$C_6$)alkyl-, or together with the nitrogen atom to which they are attached form a (4- to 8-membered)heterocycle; and R$^7$ is selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, —($C_1$-$C_6$)alkoxy-COOR$^7$, —NH—C(=O)—NH—($C_1$-$C_6$)alkyl, —NH—C(=O)-(6- to 14-membered)aryl, —NH—C(=O)—($C_1$-$C_6$)alkyl-(6- to 14-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, -(6- to 14-membered)aryl, -(6- to 14-membered) aryloxy, —($C_1$-$C_6$)alkoxy-C(O)—NR$^5$R$^6$, —NH—($C_1$-$C_6$) alkyl-C(O)—NR$^5$R$^6$, —C(O)NH—($C_1$-$C_6$)alkyl-COOR$^7$, —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$) alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$) cycloalkyl)-($C_1$-$C_6$)alkoxy-, (($C_3$-$C_{12}$)cycloalkyl)-($C_1$-$C_6$) alkoxy-($C_1$-$C_6$)alkyl-, —($C_4$-$C_{12}$)cycloalkenyl, (($C_4$-$C_{12}$) cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$) alkyl-, -(6- to 14-membered)aryl, ((6- to 14-membered)aryl)-($C_1$-$C_6$)alkyl-, ((6- to 14-membered)aryl)-($C_1$-$C_6$)alkoxy-, ((6- to 14-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$) alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-.

As used herein, compounds that bind to receptors and mimic the regulatory effects of endogenous ligands are defined as "agonists". Compounds that bind to receptors and are only partly effective as agonists are defined as "partial agonists". Compounds that bind to a receptor without producing any regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics*, 10$^{th}$ Ed. (J. G. Hardman, L. E. Limbird and A. Goodman-Gilman eds., 2001).

Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl, respectively, and preferably $^3$H, $^{11}$C, and $^{14}$C. Isotopically-labeled Compounds of the Invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds are generally described in Filer, Isotopes in the Physical and Biomedical Sciences, Vol. 1, Labeled Compounds (Part A), Chapter 6 (1987). $^{14}$C-labeled compounds can be prepared by employing starting materials having a $^{14}$C carbon.

Isotopically labeled Compounds of the Invention, as well as the pharmaceutically acceptable salts, and solvates thereof, can be used as radioligands to test for the binding of compounds to an opioid or ORL-1 receptor. For example, a radio-labeled Compound of the Invention can be used to characterize specific binding of a test or candidate compound to the receptor. Binding assays utilizing such radio-labeled compounds can provide an alternative to animal testing for the evaluation of chemical structure-activity relationships. In a non-limiting embodiment, the present invention provides a method for screening a candidate compound for the ability to bind to an opioid or ORL-1 receptor, comprising the steps of: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Compounds of the Invention disclosed herein may contain one or more asymmetric centers, thus giving rise to enantiomers, diastereomers, and other stereoisomeric forms. The present invention encompasses all such possible forms, as well as their racemic and resolved forms and mixtures thereof, and the uses thereof. The individual enantiomers may be separated according to methods known to those of ordinary skill in the art in view of the present disclosure. When the compounds described herein contain olefinic double bonds or other centers of geometric asymmetry, and unless specified otherwise, they include both E and Z geometric isomers. All tautomers are intended to be encompassed by the present invention as well.

As used herein, the term "stereoisomer" is a general term for all isomers of individual molecules that differ only in the orientation of their atoms in space. It includes enantiomers and isomers of compounds with more than one chiral center that are not minor images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active such that the enantiomer rotates the plane of polarized light in one direction and its minor image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

Compounds of the Invention encompass all salts of the disclosed compounds of Formula I. The present invention preferably includes any and all non-toxic, pharmaceutically acceptable salts of the disclosed compounds. Examples of pharmaceutically acceptable salts include inorganic and organic acid addition salts and basic salts. The pharmaceutically acceptable salts include, but are not limited to, metal salts such as sodium salt, potassium salt, cesium salt, and the like; alkaline earth metals such as calcium salt, magnesium salt and the like; organic amine salts such as triethylamine salt, pyridine salt, picoline salt, ethanolamine salt, triethanolamine salt, dicylohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention and a pharmaceutically acceptable non-toxic base such as sodium hydroxide, potassium hydroxide, choline hydroxide, sodium carbonate and the like.

Compounds of the Invention also encompass solvates of the disclosed compounds of Formula I, Formula II, Formula III, Formula IV, and Formula V. The term "solvate" as used herein is a combination, physical association and/or solvation of a compound of Formula I, Formula II, Formula III, Formula IV, or Formula V with a solvent molecule such as, e.g. a disolvate, monosolvate or hemisolvate, where the ratio of solvent molecule to compound of Formula I, Formula II, Formula III, Formula IV, or Formula V is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. A compound of Formula I, Formula II, Formula III, Formula IV, or Formula V may be present as a solvated form with a pharmaceutically acceptable solvent, such as water, methanol, ethanol, and the like, and it is intended that the invention include both solvated and unsolvated forms of Formula I, Formula II, Formula III, Formula IV, or Formula V compounds. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.*, 603-604 (2001). A typical, non-limiting, process of preparing a solvate would involve dissolving a compound of Formula I, Formula II, Formula III, Formula IV, or Formula V in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present invention also provides the use of a Compound of the Invention in the manufacture of a medicament for treating or preventing a Condition. In one embodiment, the Condition is pain, such as acute or chronic pain. In one embodiment, a Compound of the Invention has agonist activity at the μ, δ and/or κ receptors. In another embodiment a Compound of the Invention has agonist activity at the μ receptor. In another embodiment, a Compound of the Invention has antagonist activity at the ORL-1 receptor. In another embodiment, certain Compounds of the invention can stimulate one receptor (e.g., a μ, δ and/or κ agonist) and inhibit a different receptor (e.g., an ORL-1 antagonist). In another embodiment, the Compound of the Invention is an agonist at the μ receptor, and an antagonist at the ORL-1 receptor.

Synthesis of Compounds

Compounds of Formula I can be made using conventional organic synthesis in view of this disclosure, or by the illustrative methods shown in the schemes below.

Scheme A

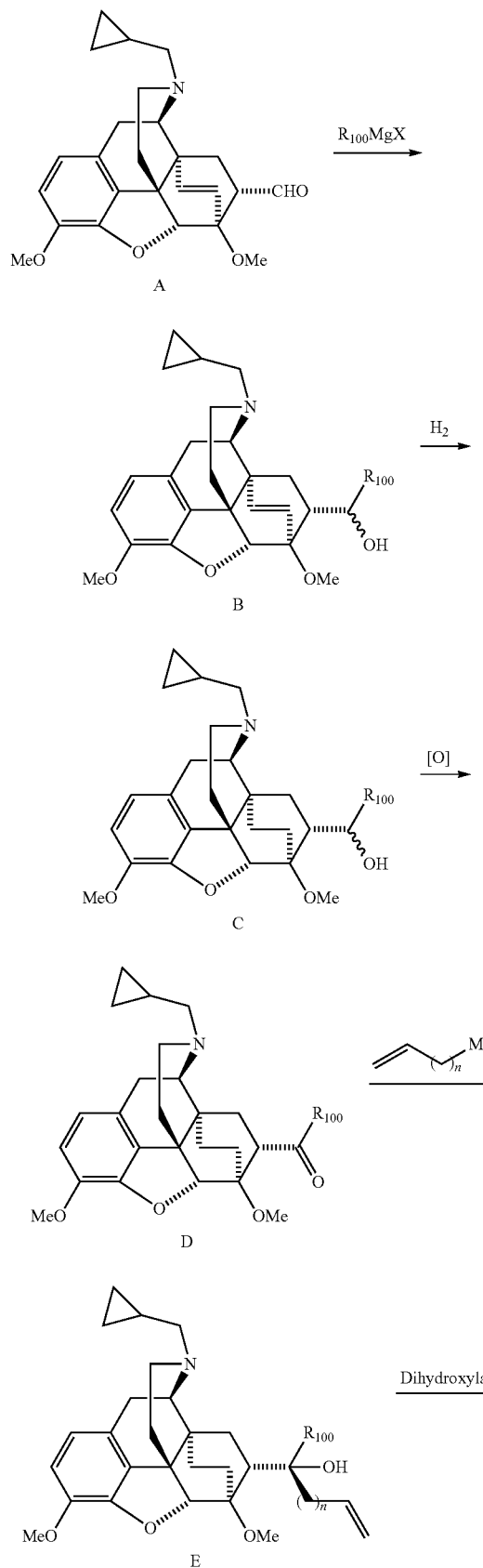

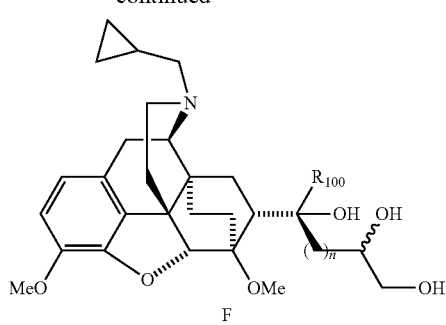

Compound A is reacted with an organometalic compound such as a Grignard reagent in a suitable solvent such as ether or THF to give alcohol B. The double bond in compound B is reduced to a single bond by appropriate reducing conditions such as hydrogenation in a suitable solvent such as ethanol or methanol with a suitable catalyst such as palladium on carbon (Pd/C) to give compound C. The alcohol group in compound C can be oxidized to the ketone D with a suitable oxidizing reagent such as Dess-Martin periodane [*Org. Synth., Coll. Vol.* 10, 2004, 696] or pyridinium chlorochromate (PCC) in a suitable solvent such as dichloromethane (DCM). The ketone D can be reacted with an olefinic organometalic compound such as an olefinic Grignard reagent in a suitable solvent such as ether or THF to give olefin E. The double bond in compound E can be converted to a diol by reaction with a suitable reagent such as osmium tetroxide with or without a co-oxidant such as N-methylmorpholine N-oxide (NMO) in a suitable solvent such as an acetone/water mixture to give compound F.

Scheme B

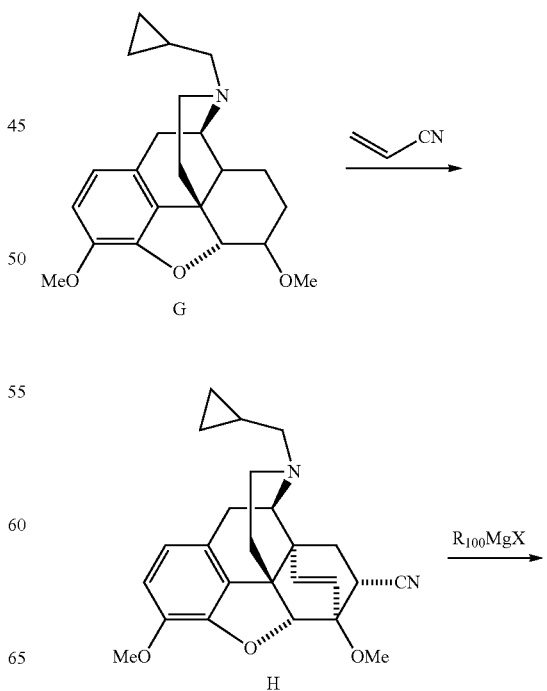

Scheme C

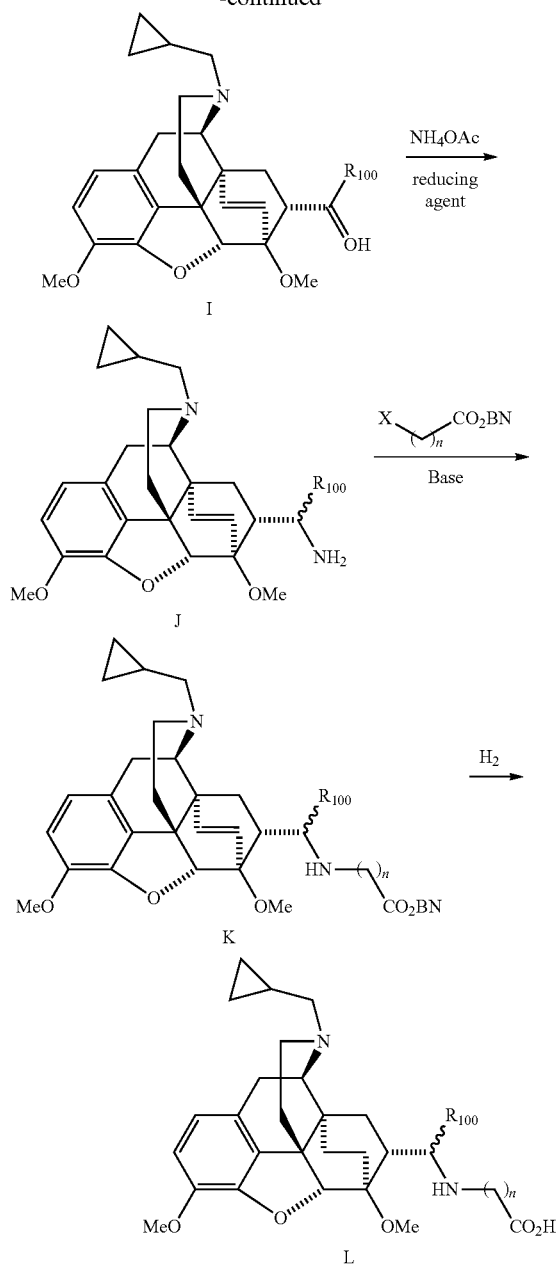

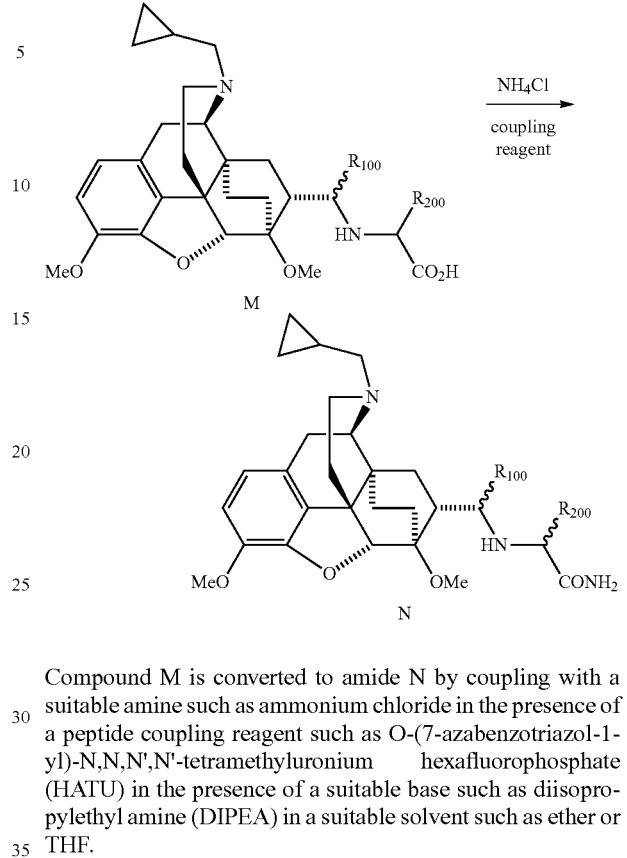

Compound M is converted to amide N by coupling with a suitable amine such as ammonium chloride in the presence of a peptide coupling reagent such as O-(7-azabenzotriazol-1-yl)-N,N,N',N'-tetramethyluronium hexafluorophosphate (HATU) in the presence of a suitable base such as diisopropylethyl amine (DIPEA) in a suitable solvent such as ether or THF.

Testing of Compounds

μ-opioid Receptor Binding Assay Procedures: Radioligand dose-displacement binding assays for μ-opioid receptors used 0.3 nM [$^3$H]-diprenorphine (Perkin Elmer, Shelton, Conn.), with 5 mg membrane protein/well in a final volume of 500 μl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hr at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 μl of ice-cold binding buffer. Filter plates were subsequently dried at 50° C. for 2-3 hours. BetaScint scintillation cocktail (Perkin Elmer, Shelton, Conn.) was added (50 μl/well), and plates were counted using a Packard Top-Count for 1 min/well. The data were analyzed using the one-site competition curve fitting functions in GraphPad PRISM™ v. 3.0 or higher (San Diego, Calif.), or an in-house function for one-site competition curve-fitting.

μ-Opioid Receptor Binding Data: Generally, the lower the Ki value, the more effective the Compounds of the Invention will be at treating or preventing pain or another Condition. Typically, the Compounds of the Invention will have a Ki (nM) of about 1000 or less for binding to μ-opioid receptors. In one embodiment the Compounds of the Invention will have a Ki (nM) of about 300 or less for binding to μ-opioid recep- Compound G is reacted with an unsaturated nitrile in a suitable solvent such as toluene at an elevated temperature such as 60-100° C. to give compound H. The nitrile in compound H is reacted with an organometalic compound such as a Grignard reagent in a suitable solvent such as benzene, ether or THF to give ketone I. Reductive amination with a suitable source of ammonia such as ammonium acetate and a suitable reducing agent such as sodium borohydride in a suitable solvent such as methanol gives amine J. Alkylation with a suitable halo benzyl ester in the presence of a suitable base such as triethyl amine (TEA) in an appropriate solvent such as ether or THF gives compound K. Reduction of the double bond and hydrogenolysis of the benzyl ester by hydrogenation in a suitable solvent such as ethanol or methanol with a suitable catalyst such as palladium on carbon (Pd/C) gives compound L.

tors. In one embodiment, Compounds of the Invention will have a Ki (nM) of about 100 or less. In another embodiment, Compounds of the Invention will have a Ki (nM) of about 10 or less. In still another embodiment, Compounds of the Invention will have a Ki (nM) of about 1 or less. In still another embodiment, Compounds of the Invention will have a Ki (nM) of about 0.1 or less.

μ-Opioid Receptor Functional Assay Procedures: [$^{35}$S]GTPγS functional assays were conducted using freshly thawed pt-receptor membranes prepared in-house from a cell line expressing recombinant μ opioid receptor in a HEK-293, CHO or U-2 OS cell background, or purchased from a commercial source (Perkin Elmer, Shelton, Conn.; or DiscovRx, Fremont, Calif.). Assay reactions were prepared by sequentially adding the following reagents to binding buffer (100 mM NaCl, 10 mM MgCl$_2$ 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, Conn.). The prepared membrane solution (190 μl/well) was transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 min at about 25° C. with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200 μl of ice-cold wash buffer (10 mM NaH$_2$PO$_4$, 10 mM Na$_2$HPO$_4$, pH 7.4). Filter plates were subsequently dried at 50° C. for 2-3 hr. BetaScint scintillation cocktail (Perkin Elmer, Shelton, Conn.) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data: μ GTP EC$_{50}$ is the concentration of a compound providing 50% of the maximal response for the compound at a μ-opioid receptor. Compounds of the Invention will typically have a μ GTP EC$_{50}$ (nM) of about 5000 or less. In certain embodiments, Compounds of the Invention will have a μ GTP EC$_{50}$ (nM) of about 2000 or less; or about 1000 or less; or about 100 or less; or about 10 or less; or about 1 or less; or about 0.1 or less.

μ GTP E$_{max}$ (%) is the maximal effect elicited by a compound relative to the effect elicited by DAMGO, a standard μ agonist. Generally, the μ GTP E$_{max}$ (%) value measures the efficacy of a compound to treat or prevent pain or other Conditions. Typically, Compounds of the Invention will have a μ GTP E$_{max}$ (%) of greater than about 10%; or greater than about 20%. In certain embodiments, Compounds of the Invention will have a μ GTP E$_{max}$ (%) of greater than about 50%; or greater than about 65%; or greater than about 75%; or greater than about 85%; or greater than about 100%.

κ-Opioid Receptor Binding Assay Procedures: Membranes from recombinant HEK-293 cells expressing the human κ opioid receptor (cloned in house) were prepared by lysing cells in ice cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at −80° C.

Radioligand dose displacement assays used 0.4 nM [$^3$H]-U69,593 (GE Healthcare, Piscataway, N.J.; 40 Ci/mmole) with 15 μg membrane protein (recombinant κ opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

κ-Opioid Receptor Binding Data: In certain embodiments, the Compounds of the Invention will have a Ki (nM) for κ receptors of about 10,000 or more (which, for purposes of this invention, is interpreted as having no binding to the κ receptors). Certain Compounds of the Invention will have a Ki (nM) of about 20,000 or less for κ receptors. In certain embodiments, Compounds of the Invention will have a Ki (nM) of about 10,000 or less; or about 5000 or less; or about 1000 or less; or about 500 or less; or about 450 or less; or about 350 or less; or about 200 or less; or about 100 or less; or about 50 or less; or about 10 or less; or about 1 or less; or about 0.1 or less.

κ-Opioid Receptor Functional Assay Procedures: Membranes from recombinant HEK-293 cells, CHO or U-2 OS cells expressing the recombinant human κ opioid receptor (κ) were prepared by lysing cells in ice cold hypotonic buffer (2.5 mM MgCl$_2$, 50 mM HEPES, pH 7.4) (10 mL/10 cm dish) followed by homogenization with a tissue grinder/Teflon pestle. Functional [$^{35}$S]GTPγS binding assays were conducted as follows. κ opioid receptor membrane solution was prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well.

κ-Opioid Receptor Functional Data: κ GTP EC$_{50}$ is the concentration of a compound providing 50% of the maximal response for the compound at a κ receptor. Certain Compounds of the Invention will have a κ GTP EC$_{50}$ (nM) of about 20,000 or less to stimulate κ opioid receptor function. In certain embodiments, Compounds of the Invention will have a κ GTP EC$_{50}$ (nM) of about 10,000 or less; or about 5000 or less; or about 2000 or less; or about 1500 or less; or about 1000 or less; or about 600 or less; or about 100 or less; or about 50 or less; or about 25 or less; or about 10 or less; or about 1 or less; or about 0.1 or less.

κ GTP $E_{max}$ (%) is the maximal effect elicited by a compound relative to the effect elicited by U69,593. Certain Compounds of the Invention will have a κ GTP $E_{max}$ (%) of greater than about 1%; or greater than about 5%; or greater than about 10%; or greater than about 20%. In certain embodiments, Compounds of the Invention will have a κ GTP $E_{max}$ (%) of greater than about 50%; or greater than about 75%; or greater than about 90%; or greater than about 100%.

δ-opioid Receptor Binding Assay Procedures: δ-opioid Receptor Binding Assay Procedures can be conducted as follows. Radioligand dose-displacement assays use 0.3 nM [$^3$H]-Naltrindole (Perkin Elmer, Shelton, Conn.; 33.0 Ci/mmole) with 5 μg membrane protein (Perkin Elmer, Shelton, Conn.) in a final volume of 500 μl binding buffer (5 mM $MgCl_2$, 5% DMSO, 50 mM Trizma base, pH 7.4). Non-specific binding is determined in the presence of 25 μM unlabeled naloxone. All reactions are performed in 96-deep well polypropylene plates for 1 hr at a temperature of about 25° C. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by five filtration washes with 500 μl ice-cold binding buffer. Filter plates are subsequently dried at 50° C. for 1-2 hours. Fifty μl/well scintillation cocktail (Perkin Elmer, Shelton, Conn.) is added and plates are counted in a Packard Top-Count for 1 min/well.

δ-Opioid Receptor Binding Data: In certain embodiments, the Compounds of the Invention will have a Ki (nM) for δ receptors of about 10,000 or more (which, for the purposes of this invention, is interpreted as having no binding to the δ receptors). Certain Compounds of the Invention will have a Ki (nM) of about 20,000 or less for δ receptors. In one embodiment, the Compounds of the Invention will have a Ki (nM) of about 10,000 or less; or of about 9000 or less. In another embodiment, the Compounds of the Invention will have a Ki (nM) of about 7500 or less; or of about 6500 or less; or of about 5000 or less; or of about 3000 or less; or of about 2500 or less. In another embodiment, the Compounds of the Invention will have a Ki (nM) of about 1000 or less; or of about 500 or less; or of about 350 or less; or of about 250 or less; or of about 100 or less; or of about 10 or less.

δ-Opioid Receptor Functional Assay Procedures: Functional [$^{35}$S]GTPγS binding assays are conducted as follows. δ opioid receptor membrane solution is prepared by sequentially adding final concentrations of 0.026 μg/μl δ membrane protein (Perkin Elmer, Shelton, Conn.), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) is transferred to 96-shallow well polypropylene plates containing 10 μl of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates are subsequently dried at 50° C. for 1-2 hours. Fifty μl/well scintillation cocktail (Perkin Elmer, Shelton, Conn.) is added and plates are counted in a Packard Top-count for 1 min/well.

δ-Opioid Receptor Functional Data: δ GTP $EC_{50}$ is the concentration of a compound providing 50% of the maximal response for the compound at a δ receptor. Certain Compounds of the Invention will have a δ GTP $EC_{50}$ (nM) of about 20,000 or less; or about 10,000 or less. In certain embodiments, the Compounds of the Invention will have a δ GTP $EC_{50}$ (nM) of about 3500 or less; or of about 1000 or less; or of about 500 or less; or of about 100 or less; or of about 90 or less; or of about 50 or less; or of about 25 or less; or of about 10 or less.

δ GTP $E_{max}$ (%) is the maximal effect elicited by a compound relative to the effect elicited by met-enkephalin. Certain Compounds of the Invention of the invention will have a δ GTP $E_{max}$ (%) of greater than about 1%; or of greater than about 5%; or of greater than about 10%. In one embodiment, the Compounds of the Invention will have a δ GTP $E_{max}$ (%) of greater than about 30%. In other embodiments, the Compounds of the Invention will have a δ GTP $E_{max}$ (%) of greater than about 50%; or of greater than about 75%; or of greater than about 90%. In another embodiment, the Compounds of the Invention will have a δ GTP $E_{max}$ (%) of about 100% or greater.

ORL-1 Receptor Binding Assay Procedure: Membranes from recombinant HEK-293 cells expressing the human opioid receptor-like receptor (ORL-1) (Perkin Elmer, Shelton, Conn.) are prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes are collected by centrifugation at 30,000×g for 15 min at 4° C. and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Radioligand binding assays (screening and dose-displacement) use 0.1 nM [$^3$H]-nociceptin (Perkin Elmer, Shelton, Conn.; 87.7 Ci/mmole) with 12 μg membrane protein in a final volume of 500 μl binding buffer (10 mM $MgCl_2$, 1 mM EDTA, 5% DMSO, 50 mM HEPES, pH 7.4). Non-specific binding is determined in the presence of 10 nM unlabeled nociceptin (American Peptide Company). All reactions are performed in 96-deep well polypropylene plates for 1 h at room temperature. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by three filtration washes with 500 μl ice-cold binding buffer. Filter plates are subsequently dried at 50° C. for 2-3 hours. Fifty μl/well scintillation cocktail (Perkin Elmer, Shelton, Conn.) is added and plates are counted in a Packard Top-Count for 1 min/well. The data from screening and dose-displacement experiments are analyzed using Microsoft Excel and the curve fitting functions in GraphPad PRISM™, v. 3.0 or higher, respectively, or an in-house function for one-site competition curve-fitting.

ORL-1 Receptor Binding Data: Certain Compounds of the Invention will have a Ki (nM) of about 1000 or less. In one embodiment, the Compounds of the Invention will have a Ki (nM) of about 500 or less. In other embodiments, the Compounds of the Invention will have a Ki (nM) of about 300 or less; or of about 100 or less; or of about 50 or less; or of about 20 or less. In yet other embodiments, the Compounds of the Invention will have a Ki (nM) of about 10 or less; or of about 1 or less; or of about 0.1 or less.

ORL-1 Receptor Functional Assay Procedure: Membranes from recombinant HEK-293 cells expressing the human opioid receptor-like (ORL-1) (Perkin Elmer, Shelton, Conn.) are prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes are collected by centrifugation at 30,000×g for 15 min at 4° C., and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at –80° C.

Functional [$^{35}$S]GTPγS binding assays are conducted as follows. ORL-1 membrane solution is prepared by sequentially adding final concentrations of 0.026 µg/µl ORL-1 membrane protein, 10 µg/ml saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 µl/well) is transferred to 96-shallow well polypropylene plates containing 10 µl of 20× concentrated stock solutions of agonist/nociceptin prepared in DMSO. Plates are incubated for 30 min at room temperature with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 µl ice-cold binding buffer (10 mM NaH$_2$PO$_4$,10 mM Na$_2$HPO$_4$, pH 7.4). Filter plates are subsequently dried at 50° C. for 2-3 hours. Fifty µl/well scintillation cocktail (Perkin Elmer, Shelton, Conn.) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting.

ORL-1 Receptor Functional Data: ORL-1 GTP EC$_{50}$ is the concentration of a compound providing 50% of the maximal response for the compound at an ORL-1 receptor. In certain embodiments, the Compounds of the Invention that have a high binding affinity (i.e. low K$_i$ value) will have an ORL-1 GTP EC$_{50}$ (nM) of greater than about 10,000 (i.e. will not stimulate at therapeutic concentrations) In certain embodiments Compounds of the Invention will have an ORL-1 GTP EC$_{50}$ (nM) of about 20,000 or less. In one embodiment, the Compounds of the Invention will have an ORL-1 GTP EC$_{50}$ (nM) of about 10,000 or less; or of about 5000 or less; or of about 1000 or less. In still other embodiments, the Compounds of the Invention will have an ORL-1 GTP EC$_{50}$ (nM) of about 100 or less; or of about 10 or less; or of about 1 or less; or of about 0.1 or less.

ORL-1 GTP E$_{max}$% is the maximal effect elicited by a compound relative to the effect elicited by nociceptin, a standard ORL-1 agonist. In certain embodiments, Compounds of the Invention will have an ORL-1 GTP E$_{max}$ of less than 10% (which, for the purposes of this invention, is interpreted as having antagonist activity at ORL-1 receptors). Certain Compounds of the Invention will have an ORL-1 GTP E$_{max}$ (%) of greater than 1%; or of greater than 5%; or of greater than 10%. In other embodiments the Compounds of the Invention will have an ORL-1 GTP E$_{max}$ of greater than 20%; or of greater than 50%; or of greater than 75%; or of greater than 88%; or of greater than 100%.

In Vivo Assays for Prevention or Treatment of Pain

Test Animals: Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain: To assess the actions of a Compound of the Invention for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the Invention. Data are expressed as tail flick latency(s) and the percentage of the maximal possible effect (% MPE), i.e., 20 seconds, is calculated as follows:

$$\%MPE = \frac{[(\text{post administration latency}) - (\text{pre-administration latency})]}{(20\,s - \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

To assess the actions of a Compound of the Invention for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). A rat is placed into the cylinder on the hot plate apparatus for a maximum duration of 30 s, or until it exhibits a nocifensive behavior (behavioral endpoint), at which time it is removed from the hot plate, and response latency recorded. Hot plate latencies are measured immediately before (pre-treatment) and 1, 3, and 5 hours following administration of a Compound of the Invention. The nocifensive behavioral endpoint is defined as any of the following: 1) paw withdrawal, either as a sustained lift or with shaking or licking; 2) alternating foot lifting; 3) escape or attempted escape from the testing device; or 4) vocalization. Data are expressed as response latency(s) and the percentage of the maximal possible effect is calculated as described above for the tail flick test. The hot plate test is described in G. Woolfe and A. D. Macdonald, *J. Pharmacol. Exp. Ther.* 80:300-307 (1944).

Inflammatory Pain: To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 µL intraplantar injection of 50% FCA. Prior to injection of FCA (baseline) and 24 hours post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\% \text{Reversal} = \frac{[(\text{post administration } PWT) - (\text{pre-administration } PWT)]}{[(\text{baseline } PWT) - (\text{pre-administration } PWT)]}$$

Neuropathic Pain: To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," Pain 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," Pain 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," Pharmacol. Biochem. and Behavior 31:451-455 (1988). The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," Pain 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression: To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., 2000 Intensive Care Med. (26) 585-591).

Assessment of Gastric Motility: Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions

Due to their activity, the Compounds of the Invention are advantageously useful in human and veterinary medicine. As described above, the Compounds of the Invention are useful for treating or preventing a Condition in an animal (a human patient or non-human subject) in need thereof. The Compounds of the Invention can be administered to any animal requiring modulation of the opioid and/or ORL-1 receptors.

When administered to an animal, a Compound of the Invention can be administered as a component of a pharmaceutical composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, sustained-release formulations, controlled-release formulations, suppositories, aerosols, sprays, or any other form suitable for use. In one embodiment, the composition is in the form of a capsule (see, e.g., U.S. Pat. No. 5,698,155).

Pharmaceutical compositions of the invention preferably comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986). Other examples of suitable pharmaceutical excipients are described in *Remington's Pharmaceutical Sciences* 1447-1676 (Alfonso R. Gennaro ed., 19th ed. 1995), incorporated herein by reference.

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a Compound of the Invention is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocalne to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the Invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the Invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release, Vol. 2, Applications and Evaluation*, R. S. Langer and D. L. Wise eds., CRC Press (1984). Other controlled- or sustained-release systems that are discussed in the review by Langer, *Science* 249:1527-1533 (1990) can be selected for use according to the present invention. In one embodiment, a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each animal's circumstances. Variations in dosing may occur depending upon typical factors such as the weight, age, gender and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Compound of the Invention, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Compound of the Invention is administered, the effective dosage amounts correspond to the total amount administered.

Where a cell capable of expressing the ORL-1 receptor is contacted with a Compound of the Invention in vitro, the amount effective for inhibiting or activating the ORL-1 receptor function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the µ-opioid receptors is contacted with a Compound of the Invention in vitro, the amount effective for inhibiting or activating the µ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the δ-opioid receptors is contacted with a Compound of the Invention in vitro, the amount effective for inhibiting or activating the δ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the κ-opioid receptors is contacted with a Compound of the Invention in vitro, the amount effective for inhibiting or activating the κ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

The Compounds of the Invention can be assayed in vitro or in vivo for the desired therapeutic or prophylactic activity prior to use in humans. Animal model systems can be used to demonstrate safety and efficacy. Certain Compounds of the Invention will have an $ED_{50}$ for treating inflammatory pain ranging from about 0.5 mg/kg to about 20 mg/kg. Certain Compounds of the Invention will produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the invention, methods for treating or preventing a Condition in an animal in need thereof can further comprise co-administering to the animal an effective amount of a second therapeutic agent in addition to a Compound of the Invention (i.e., a first therapeutic agent). An effective amount of the second therapeutic agent will be known or determinable by a medical practitioner in view of this disclosure and published clinical studies. In one embodiment of the invention, where a second therapeutic agent is administered to an animal for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Insel, *Analgesic-Antipyretic and Anti-inflammatory Agents and Drugs Employed in the Treatment of Gout, in Goodman & Gilman's The Pharmacological Basis of Therapeutics* 617-57 (Perry B. Molinhoff and Raymond W. Ruddon eds., $9^{th}$ ed 1996); and Glen R. Hanson, *Analgesic, Antipyretic and Anti-Inflammatory Drugs in Remington: The Science and Practice of Pharmacy Vol IA* 1196-1221 (A. R. Gennaro ed. $19^{th}$ ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexyline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpiclone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the invention is prepared by a method comprising admixing a Compound of the Invention (or a pharmaceutically acceptable salt, prodrug or solvate thereof) with a pharmaceutically acceptable carrier or excipient. Admixing can be accomplished using methods known for admixing a compound (or derivative) and a pharmaceutically acceptable carrier or excipient. In one embodiment, the Compound of the Invention (or pharmaceutically acceptable salt, prodrug or solvate thereof) is present in the composition in an effective amount.

EXAMPLES

Example 1

(4R)-4-((4R,4aS,6R,7R,7aR,12bS)-3-(cyclopropylmethyl)-7,9-dimethoxy-1,2,3,4,5,6,7,7a-octahydro-4-a, 7-ethano-4,12-methanobenzofuro[3,2-e]isoquinolin-6-yl)-4-phenylbutane-1,2,4-triol (Compound 6)

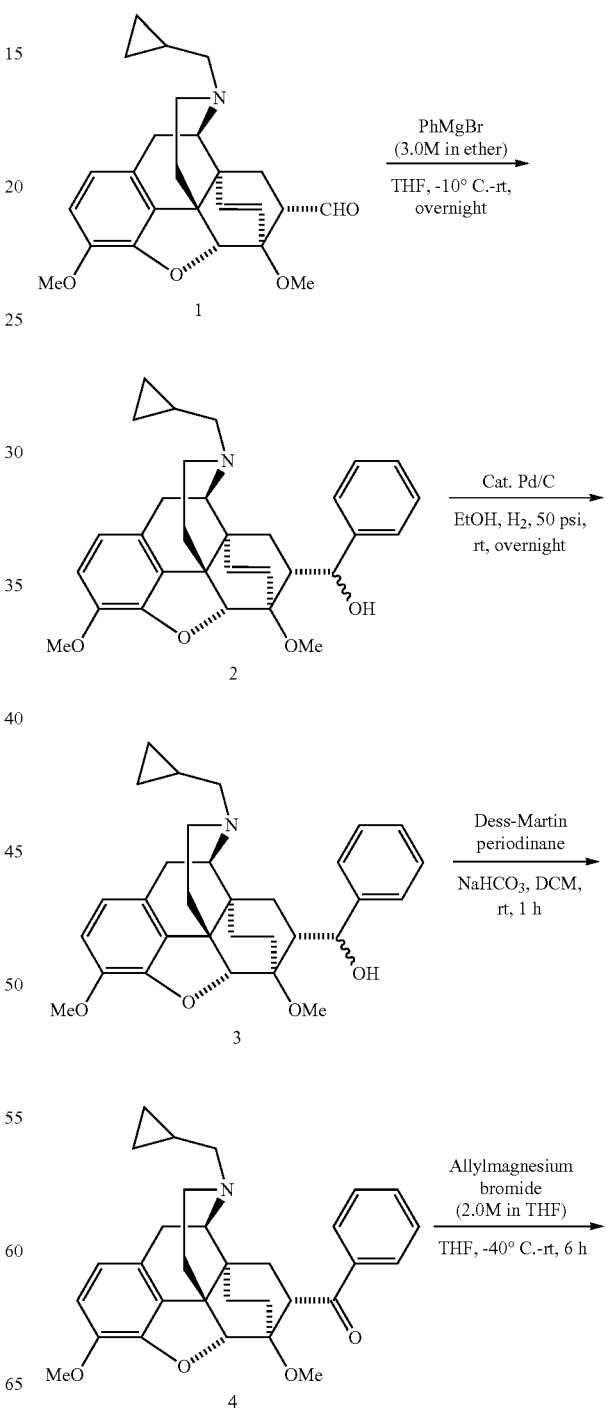

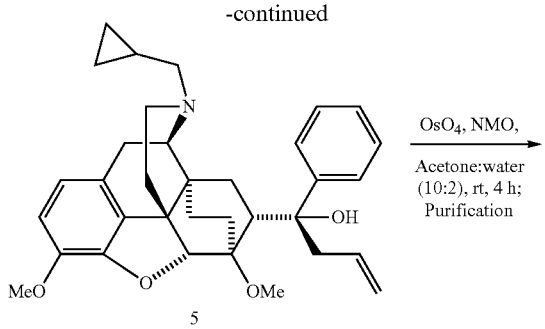

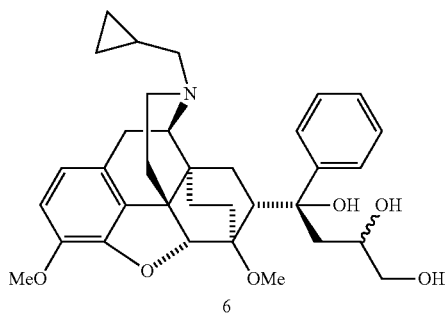

Phenylmagnesium bromide (2.7 mL, 8.1 mmol, 3.0 M solution in ether) was added to a solution of 1 (2.2 g, 5.4 mmol) in THF (25 mL, anhydrous) at −10° C. under a nitrogen atmosphere. The resulting mixture was allowed to warm to room temperature overnight. The reaction mixture was quenched with ice water, extracted with ethyl acetate (EtOAc), dried over sodium sulfate ($Na_2SO_4$), filtered and concentrated. The crude 2 (2.8 g, quantitative yield, as a mixture of diastereomers) was used for the next reaction.

LC/MS, m/z=486 [M+H]$^+$ (Calc: 485).

A mixture of 2 (2.8 g, 5.4 mmol) and 5% Palladium on carbon (5% Pd/C) in absolute ethanol (EtOH) (30 mL) was hydrogenated at 50 psi of hydrogen overnight. The mixture was filtered through a Celite pad and concentrated. The crude 3 (2.9 g, quantitative yield, as a mixture of diastereomers) was used for the next reaction.

LC/MS, m/z=488 [M+H]$^+$ (Calc: 487).

Dess-Martin periodinane (2.1 g, 4.9 mmol) was added to a suspension of 3 (1.2 g, 2.5 mmol) and sodium bicarbonate ($NaHCO_3$) (2.5 g, 29.5 mmol) at room temperature. The reaction mixture quenched with saturated aqueous sodium sulfite ($Na_2SO_3$) after stifling at room temperature for 1 h. The resulting mixture was stirred vigorously for 15 min. Saturated aqueous sodium bicarbonate ($NaHCO_3$) was added, and the mixture was extracted with EtOAc. The organic layer was dried over $Na_2SO_4$, filtered and concentrated. The crude material was purified by flash chromatography ($SiO_2$, 10-50% EtOAc/hexanes) to obtain compound 4 (0.8 g, 67% yield) as a pale yellow foam.

LC/MS, m/z=486 [M+H]$^+$ (Calc: 485).

Allylmagnesium bromide (0.23 mL, 0.45 mmol, 2.0 M solution in THF) was added to a solution of 4 (0.2 g, 0.41 mmol) in THF (5 mL) at −40° C. under a nitrogen atmosphere. The mixture was allowed to warm to room temperature over 6 h. The mixture was cooled in an ice-bath, quenched with saturated aqueous ammonium chloride ($NH_4Cl$) and extracted with EtOAc. The organic layer was dried over $Na_2SO_4$, filtered and concentrated. The crude 5 (0.24 g, quantitative yield) was used for the next reaction.

LC/MS, m/z=528 [M+H]$^+$ (Calc: 527).

Osmium tetraoxide (0.24 mL, 0.04 mmol, 2% aqueous solution) was added to a solution of 5 (0.2 g, 0.38 mmol) in acetone/water (10:2 mL). After 10 min N-methylmorpholine-N-oxide (0.06 g, 0.46 mmol) was added. The reaction was stirred at room temperature for 4 h. Most of the acetone was evaporated and the mixture was partitioned between chloroform ($CHCl_3$) and saturated $NaHCO_3$. The organic layer was dried over $Na_2SO_4$, filtered and concentrated. The crude material was purified twice by flash chromatography ($SiO_2$, 10-100% EtOAc/hexanes). Final purification was achieved by reverse phase chromatography (C18, acetonitrile/water with 0.1% TFA, 0-95%) to obtain Compound 6 (24.7 mg) as the trifluoroacetate (TFA) salt.

$^1$H NMR (300 MHz, DMSO-d$_6$) δ ppm 8.42 (br s, 1H), 7.52 (d, J=7.4 Hz, 2H), 7.26 (m, 2H), 7.14 (m, 1H), 6.81 (2d, J=7.2 hz, 1H), 6.64 (d, J=7.2 Hz, 1H), 5.52 and 5.41 (bs, 1H), 4.51 (s, 1H), 3.88 (d, J=6.3 Hz, 1H), 3.73 (s, 3H), 3.54-3.10 (m, 6H), 2.92-2.58 (m., 5H), 2.54 (m, 1H), 2.40 (m, 1H), 2.34-2.17 (m, 2H), 2.11 (m, 1H), 1.95-1.80 (m, 2H), 1.60 (m, 1H); 1.18-0.84 (m, 2H), 0.77-0.58 (m, 2H), 0.54-0.32 (m, 3H).

LC/MS, m/z=562 [M+H]$^+$ (Calc: 561).

Example 2

2-(((S)-((4 R,4 aS,6 R,7 R,7 aR,12 bS)-3-(cyclopropylmethyl)-7,9-dimethoxy-1,2,3,4,5,6,7,7a-octahydro-4-a,7-ethano-4,12-methanobenzofuro[3,2-e]isoquinolin-6-yl)(phenyl)methyl)amino)acetic acid (Compound 12)

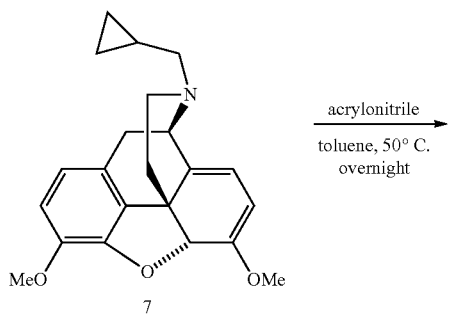

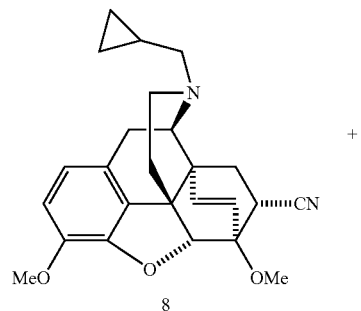

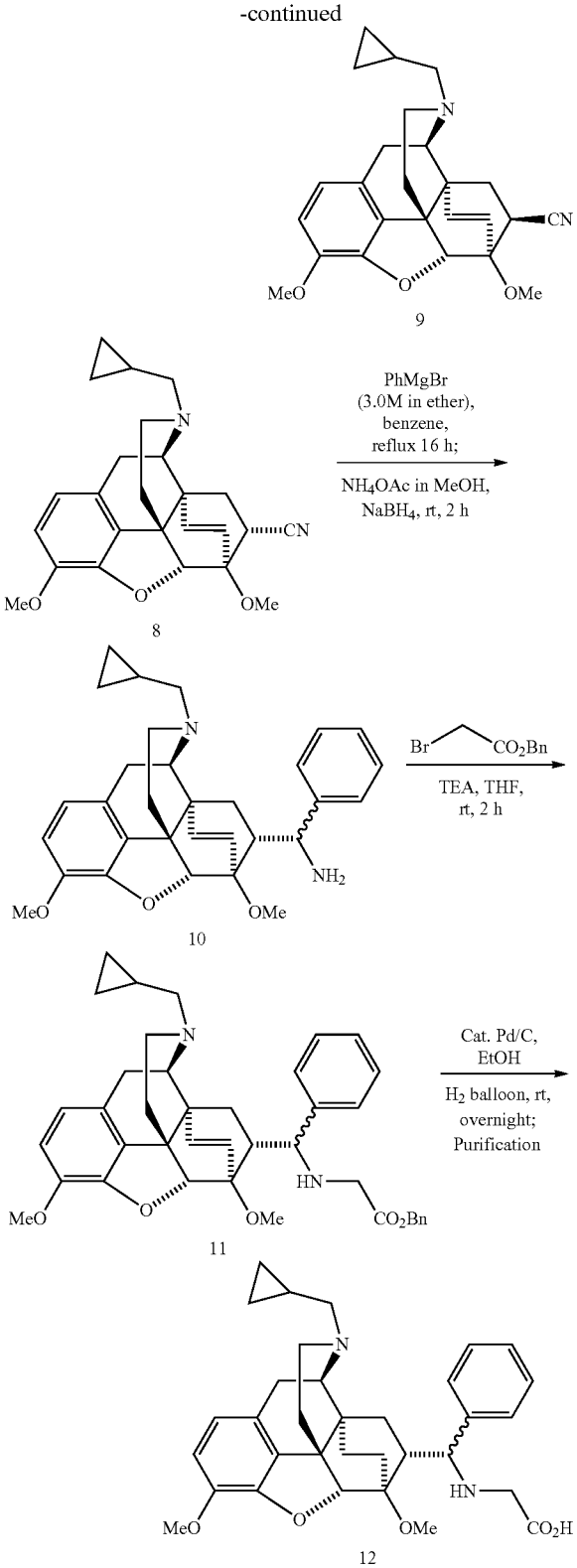

LC/MS, m/z=404 [M+H]+ (Calc: 403).

Phenylmagnesium bromide (1.15 mL, 3.4 mmol, 3.0 M solution in ether) was added to a solution of 8 (1.39 g, 3.4 mmol) in benzene (30 mL, anhydrous). The resulting mixture was heated to reflux overnight under a nitrogen atmosphere. A solution of ammonium acetate (5.9 g, 68.0 mmol) in methanol (20 mL) was added and the mixture was stirred at room temperature for 1 h. Sodium borohydride (1.2 g. 34.0 mmol) was added and the stirring continued for 2 h. The mixture was concentrated. The residue was partitioned between saturated aqueous NaHCO$_3$ and CHCl$_3$. The organic layer was dried over Na$_2$SO$_4$, filtered and concentrated. Purification of the crude material by flash chromatography (SiO$_2$, 10-50% EtOAc/hexanes) yielded 10 (0.49 g, 31% yield).

$^1$H NMR (300 MHz, CDCl$_3$) δ ppm: 7.34-7.16 (m, 5H), 6.58 (d, J=7.4 Hz, 1H), 6.44 (m, 1H), 5.79 and 5.62 (2d, J=7.4 Hz, 1H), 5.32 and 5.26 (2d, J=7.4 Hz, 1H), 4.60 (s, 1H), 3.84-3.62 (m, 9H), 3.51-3.42 (m, 2H), 3.28 (d, J=6.2 Hz, 1H), 3.10 and 2.82 (2m, 1H), 3.00 (d, J=14.1 Hz, 1H), 2.62 (m., 1H), 2.54-2.20 (m, 6H), 2.01-1.40 (m, 5H), 1.21 and 1.13 (2d, J=6.9 and 7.1 Hz, 3H), 0.69 (m, 2H), 0.41 (m, 2H), 0.002 (m, 2H).

LC/MS, m/z=485 [M+H]+ (Calc: 484).

Triethylamine (21 μL, 0.15 mmol) was added to a solution of 10 (25 mg, 0.05 mmol) and benzyl bromoacetate (16 μL, 0.10 mmol) in THF (1 mL, anhydrous). The mixture was stirred at room temperature for 2 h and concentrated. Purification of the crude material by flash chromatography (SiO$_2$, 10-50% EtOAc/hexanes) yielded 11 (29 mg, 91% yield).

LC/MS, m/z=633 [M+H]+ (Calc: 632).

A mixture of 5 (29 mg, 0.05 mmol) and 5% Pd/C in absolute ethanol (5 mL) was hydrogenated at room temperature overnight under 50 psi of hydrogen. The mixture filtered through a Celite pad. The filtrate was concentrated and the crude material was purified by reverse phase chromatography (C18, acetonitrile/water with 0.1% TFA, 0-95%) to obtain Compound 12 (12.4 mg) as the di-TFA salt.

$^1$H NMR (300 MHz, D$_2$O) δ ppm: 7.50 (bs, 5H), 6.98 (m, 1H), 6.79 (m, 1H), 4.84 (s, 1H), 4.51 (m, 1H), 3.86 (m, 4H), 3.60 (s, 3H), 3.40-2.68 (m, 8H), 2.22 (m., 2H), 2.04 (m, 1H), 1.85 (m, 2H), 1.30 (m, 1H), 1.05 (m, 1H), 0.81 (m, 2H), 0.61-0.52 (m, 2H), 0.29-0.18 (m, 2H).

LC/MS, m/z=545 [M+H]+ (Calc: 544).

In a similar manner, 2-(((S)-((4 R,4 aS,6 R,7 R,7 aR,12 bS)-3-(cyclopropylmethyl)-7,9-dimethoxy-1,2,3,4,5,6,7,7a-octahydro-4-a,7-ethano-4,12-methanobenzofuro[3,2-e]isoquinolin-6-yl)(phenyl)methyl)amino)propanoic acid (Compound 13) was prepared from 10 using benzyl 2-bromopropionate rather than benzyl bromoacetate.

$^1$H NMR (300 MHz, D$_2$O) δ ppm: (mixture of diastereomers) 9.40 (bs, 1H), 8.41 (bs, 1H), 7.73-7.41 (m, 5H), 6.91 (d, J=8.4 Hz, 1H), 6.69 (d, J=8.4 Hz, 1H), 4.71-4.61 (m, 3H), 3.87 (m, 3H), 3.75 (m, 2H), 3.58 (s, 3H), 3.56 (m, 2H), 3.32-3.22 (m., 3H), 3.00-2.64 (m, 4H), 2.35-2.14 (m, 2H), 2.00-1.71 (m, 2H), 1.62 (m, 1H), 1.45 (d, J=7.0 Hz, 1H), 1.23 (m, 1H), 0.89 (m, 3H), 0.73-0.47 (m, 3H), 0.29 (m, 2H).

LC/MS, m/z=599 [M+H]+ (Calc: 598).

In a similar manner, 2-(((S)-((4 R,4 aS,6 R,7 R,7 aR,12 bS)-3-(cyclopropylmethyl)-7,9-dimethoxy-1,2,3,4,5,6,7,7a-octahydro-4-a,7-ethano-4,12-methanobenzofuro[3,2-e]isoquinolin-6-yl)(phenyl)methyl)amino)-2-phenylacetic acid (Compound 15) was prepared from 10 using benzyl 2-phenyl-2-bromoacetate rather than benzyl bromoacetate.

$^1$H NMR (301 MHz, D$_2$O) δ ppm: (mixture of diastereomers) 8.30 (bs, 1H), 7.60-7.51 (m, 2H), 7.46-7.37 (m, 3H), 7.35-7.24 (m, 3H), 7.01-6.90 (m, 2H), 6.90 (d, J=8.5 Hz, 1H), 6.69 (d, J=8.0 Hz, 1H), 4.72 (s, 1H), 4.50 (m, 1H), 4.20 (m, Acrylonitrile (20 mL) was added to a solution of 2 (5.3 g, 15.0 mmol) in toluene (100 mL, anhydrous). The mixture was heated at 50° C. overnight. The reaction mixture was concentrated. Purification of the crude material by flash chromatography (SiO$_2$, 10-25% EtOAc/hexanes) yielded 8 (2.3 g, 37% yield) and 9 (1.92 g, 31% yield).

2H), 3.82 (s, 3H), 3.74 (m, 1H), 3.58 (s, 3H), 3.32-3.15 (m, 3H), 3.00-2.66 (m., 4H), 2.45 (m, 1H), 2.26-2.10 (m, 2H), 1.91-1.80 (m, 2H), 1.50 (m, 1H), 1.32-0.84 (m, 4H), 0.74-0.50 (m, 3H), 0.28 (m, 2H).

LC/MS, m/z=621 [M+H]$^+$ (Calc: 620).

Example 3

2-(((S)-((4 R,4 aS,6 R,7 R,7 aR,12 bS)-3-(cyclopropylmethyl)-7,9-dimethoxy-1,2,3,4,5,6,7,7a-octahydro-4-a,7-ethano-4,12-methanobenzofuro[3,2-e]isoquinolin-6-yl)(phenyl)methyl)amino)propanamide (Compound 14)

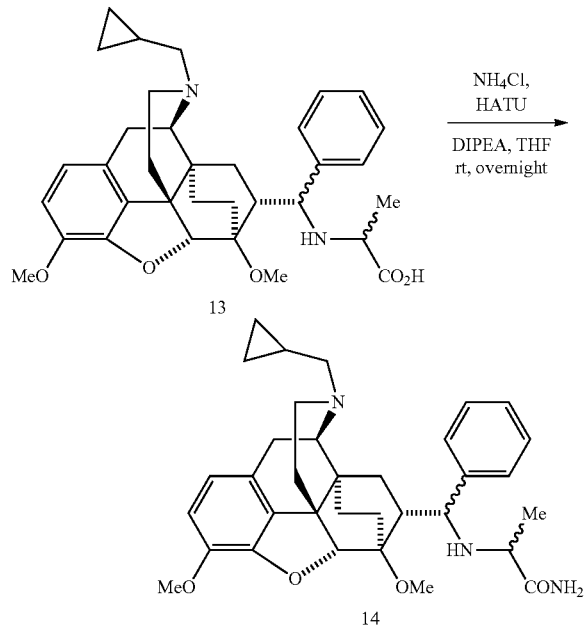

2-(7-Aza-1H-benzotriazole-1-yl)-1,1,3,3-tetramethyluronium hexafluorophosphate (HATU) (Sigma Aldrich) (86 mg, 0.23 mmol) was added to a solution of 13 (82 mg, 0.15 mmol) in THF (6.0 mL). After 10 min NH$_4$Cl (32 mg, 0.6 mmol) and diisopropylethylamine (DIPEA) (131 µl, 0.75 mmol) was added. The resulting mixture was stirred overnight at room temperature. The reaction was quenched with water and extracted with CHCl$_3$. The organic layer was dried over Na$_2$SO$_4$, filtered and concentrated. The crude material was purified by reverse phase chromatography (C18, acetonitrile/water with 0.1% TFA, 0-95%) to obtain Compound 14 (30 mg) as the di-TFA salt.

$^1$H NMR (300 MHz, D$_2$O) δ ppm: 9.34 (bs, 2H), 8.70 and 8.48 (2bs, 1H), 7.89-7.49 (m, 7H), 6.90 (d, J=8.3 Hz, 1H), 6.69 (d, J=8.2 Hz, 1H), 4.75-4.53 (m, 2H), 3.82 (m, 3H), 3.73 (m, 1H), 3.58 (s, 3H), 3.48 (m, 1H), 3.40-3.15 (m., 3H), 2.93-2.72 (m, 4H), 2.49-2.14 (m, 2H), 1.94-1.80 (m, 2H), 1.62 (m, 1H), 1.43 (d, J=6.9 Hz, 1H), 1.29 (m, 1H), 0.97 and 0.95 (2s, 3H), 0.89 (m, 2H), 0.78-0.42 (m, 3H), 0.28 (m, 2H).

LC/MS, m/z=558 [M+H]$^+$ (Calc: 557).

In a similar manner, (R)-2-(((S)-((4 R,4 aS,6 R,7 R,7 aR,12 bS)-3-(cyclopropylmethyl)-7,9-dimethoxy-1,2,3,4,5,6,7,7a-octahydro-4-a,7-ethano-4,12-methanobenzofuro[3,2-e]isoquinolin-6-yl)(phenyl)methyl)amino)-2-phenylacetamide (Compound 16) and (S)-2-(((S)-((4R,4 aS,6 R,7 R,7 aR,12 bS)-3-(cyclopropylmethyl)-7,9-dimethoxy-1,2,3,4,5,6,7,7a- octahydro-4-a,7-ethano-4,12-methanobenzofuro[3,2-d]soquinolin-6-yl)(phenyl)methyl)amino)-2-phenylacetamide (Compound 17) were prepared from 15 and separated by reverse phase chromatography (C18, acetonitrile/water with 0.1% TFA, 0-95%) to obtain Compound 16 (20.1 mg) and Compound 17 (6.5 mg) as their di-TFA salts.

Compound 16;

$^1$H NMR (300 MHz, DMSO-D6) δ ppm: 9.87 (bs, 1H), 9.70 (bs, 1H), 8.47 (bs, 1H), 8.03 (bs, 1H), 7.87 (bs, 1H), 7.66-7.38 (m, 8H), 6.98 (m, 2H), 6.93 (d, J=8.3 Hz, 1H), 6.70 (d, J=7.7 Hz, 1H), 4.66 (s, 1H), 4.57 (m, 1H), 4.30 (m, 1H), 3.84 (s, 3H), 3.76 (m, 1H), 3.67 (s, 3H), 3.32-3.16 (m, 3H), 2.92-2.72 (m., 4H), 2.33-2.07 (m, 2H), 2.00-1.84 (m, 2H), 1.71 (m, 1H), 1.38 (m, 1H), 1.01-0.88 (m, 2H), 0.80-0.43 (m, 3H), 0.28 (m, 2H).

LC/MS, m/z=620 [M+H]$^+$ (Calc: 619).

Compound 17;

$^1$H NMR (300 MHz, DMSO-D6) δ ppm: 10.30 (bs, 1H), 9.50 (bs, 1H), 8.31 (bs, 1H), 7.90 (bs, 1H), 7.80 (bs, 1H), 7.51 (m, 7H), 7.28 (m, 2H), 6.90 (d, J=8.2 Hz, 1H), 6.69 (d, J=8.2 Hz, 1H), 4.82 (s, 1H), 4.24 (m, 1H), 3.82 (s, 3H), 3.76 (m, 1H), 3.67 (s, 3H), 3.60 (m, 1H), 3.31-3.22 (m, 3H), 2.97-2.81 (m., 2H), 2.78-2.62 (m, 2H), 2.29-2.13 (m, 2H), 1.91 (m, 1H), 1.52 (m, 1H), 1.24-1.00 (m, 2H), 0.82-0.69 (m, 2H), 0.60-0.31 (m, 3H), 0.28 (m, 2H).

LC/MS, m/z=620 [M+H]$^+$ (Calc: 619).

Example 4

The following Tables provide results on the efficacy of binding and activity response of exemplified Compounds of the Invention at the µ- and κ-opioid receptors.

In TABLE 1, binding affinity of certain Compounds of the Invention to the µ-, and κ-opioid receptors in HEK-293 or CHO cells was determined as described above.

In TABLE 2, activity response of certain Compounds of the Invention at the µ- and κ-opioid receptors using HEK-293 or CHO cells was determined as described above for functional assays.

In TABLE 2A, activity response of certain Compounds of the Invention at the µ- and κ-opioid receptors using U-2 OS cells was determined as described above for functional assays.

In TABLE 3, the structure of the exemplified compounds is shown.

TABLE 1

| Binding Affinity of Buprenorphine Analog Compounds | | |
|---|---|---|
| Ref. | Ki (nM) | |
| No. | µ | κ |
| 6 | 49.88 ± 19.54 | 12.89 ± 1.94 |
| 12 | | 52.21 ± 11.99 |
| 13 | | 138.42 ± 11.32 |
| 14 | 77.05 ± 18.99 | 40.13 ± 10.54 |
| 15 | 278.49 ± 101.65 | 51.34 ± 5.77 |
| 16 | 122.72 ± 24.43 | 21.82 ± 3.53 |

TABLE 2

Activity Response of Buprenorphine Analog Compounds in HEK-293 or CHO Cells

| | GTPγS ($EC_{50}$: nM, $E_{max}$: %) | | | |
|---|---|---|---|---|
| Ref | μ | | κ | |
| No. | $EC_{50}$ | $E_{max}$ | $EC_{50}$ | $E_{max}$ |
| 6 | 196.39 ± 54.81 | 41.75 ± 3.12 | 122.29 ± 13.12 | 33.67 ± 1.86 |
| 12 | 173.59 ± 20.31 | 83.50 ± 5.25 | 744.83 ± 116.18 | 52.25 ± 1.93 |
| 13 | 379.19 ± 94.61 | 40.67 ± 2.91 | 1644.98 ± 190.35 | 43.33 ± 2.33 |
| 14 | 456.60 ± 114.15 | 32.75 ± 1.89 | 289.22 ± 52.06 | 61.67 ± 6.98 |
| 15 | 656.13 ± 70.38 | 45.33 ± 0.88 | 1769.34 ± 491.74 | 51.00 ± 3.06 |
| 16 | 15035.73 ± 1326.52 | 23.67 ± 1.76 | 771.49 ± 131.82 | 70.67 ± 3.71 |
| 17 | 4982.97 ± 395.35 | 67.67 ± 1.76 | | |

TABLE 2A

Activity Response of Benzomorphan Analog Compounds in U-2 OS Cells

| | GTPγS ($EC_{50}$: nM, $E_{max}$: %) | | | |
|---|---|---|---|---|
| Ref | μ | | κ | |
| No. | $EC_{50}$ | $E_{max}$ | $EC_{50}$ | $E_{max}$ |
| 13 | 172.50 ± 3.57 | 38.99 ± 4.04 | 398.80 ± 53.20 | 102.00 ± 4.04 |
| 14 | 53.00 ± 7.46 | 43.70 ± 2.33 | 68.30 ± 8.48 | 102.30 ± 4.37 |

TABLE 3

Exemplified Compounds

| Ref. No. | Compound | |
|---|---|---|
| 6 | 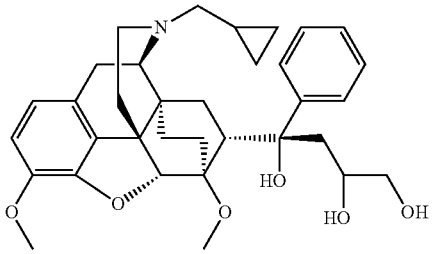 [SMILES: COc1ccc2c3c1O[C@H]1[C@@]4(OC)CC[C@@]5(C[C@@H]4[C@](O)(CC(O)CO)c4ccccc4)[C@@H](C2)N(CC2CC2)CC[C@]315] | (4R)-4-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)-4-phenylbutane-1,2,4-triol |
| 12 | 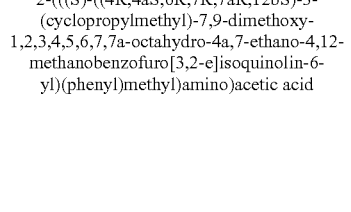 | 2-(((S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)(phenyl)methyl)amino)acetic acid |
| 13 | 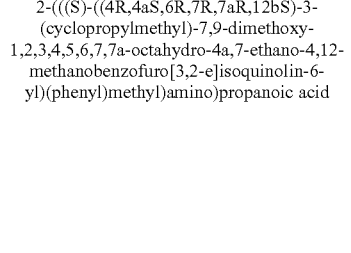 | 2-(((S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)(phenyl)methyl)amino)propanoic acid |

TABLE 3-continued

Exemplified Compounds

| Ref. No. | Compound | |
|---|---|---|
| 14 | 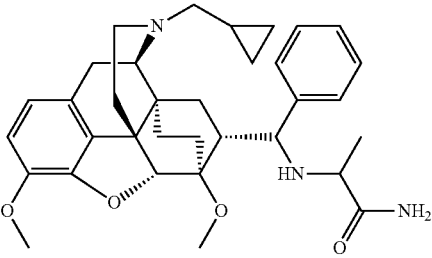 [SMILES: COc1ccc2c3c1O[C@H]1[C@@]4(OC)CC[C@@]5(C[C@@H]4C(NC(C)C(N)=O)c4ccccc4)[C@@H](C2)N(CC2CC2)CC[C@]315] | 2-(((S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)(phenyl)methyl)amino)propanamide |
| 15 | 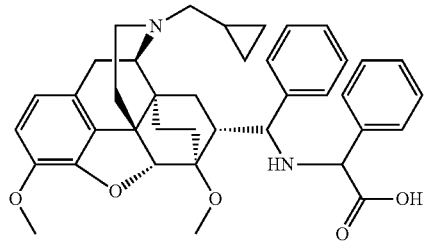 [SMILES: COc1ccc2c3c1O[C@H]1[C@@]4(OC)CC[C@@]5(C[C@@H]4C(NC(C(=O)O)c4ccccc4)c4ccccc4)[C@@H](C2)N(CC2CC2)CC[C@]315] | 2-(((S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)(phenyl)methyl)amino)-2-phenylacetic acid |
| 16 | 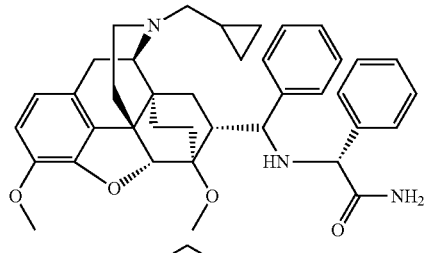 | (R)-2-(((S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)(phenyl)methyl)amino)-2-phenylacetamide |
| 17 | 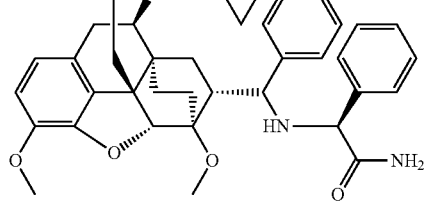 | (S)-2-(((S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)(phenyl)methyl)amino)-2-phenylacetamide |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

What is claimed is:
1. A compound of Formula I:

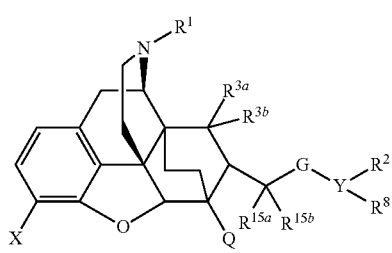

(I)

wherein
$R^1$ is selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(6- to 14-membered)aryl, ((6- to14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents each independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —CONR$^9$R$^{10}$, —NR$^9$COR$^{10}$, —SR$^9$, -(5- to 12-membered)carbocyclic ring, —(5- to 12-membered)heterocycle, phenyl, and benzyl;
$R^2$ and $R^8$ are each independently selected from the group consisting of hydrogen, —($C_1$-$C_{10}$)alkyl, —($C_2$-$C_{12}$)alkenyl, —($C_2$-$C_{12}$)alkynyl, —CONR$^5$R$^6$, —COOR$^7$, -(6- to 14-membered)aryl, ((6- to 14-membered)aryl)-($C_1$-$C_6$)alkyl-, -(5- to 12-membered)heteroaryl, and ((5- to 12-membered)heteroaryl)-($C_1$-$C_6$)alkyl-; each of which is optionally substituted with 1, 2, or 3 substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)—CO—($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-$R^{14}$, —CN, —SH, —OR$^4$, —CONR$^5$R$^6$, —($C_1$-$C_6$alkyl)—CO—NR$^5$R$^6$, —COOR$^7$, and -($C_1$-$C_6$)alkyl-CO—OR$^7$;

$R^{3a}$ and $R^{3b}$ are each independently selected from the group consisting of hydrogen, —($C_1$-$C_{10}$)alkyl, —($C_2$-$C_{10}$)alkenyl, —($C_2$-$C_{10}$)alkynyl, —CONR$^5$R$^6$, and —COOR$^7$, or together form (=O);

$R^4$ is selected from the group consisting of —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, -(6- to 14-membered)aryl, ((6- to 14-membered)aryl) -($C_1$-$C_6$)alkyl-, -(5- to 12-membered)heteroaryl, and ((5- to 12-membered)heteroaryl)-($C_1$-$C_6$)alkyl-;

$R^5$ and $R^6$ are each independently selected from the group consisting of hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, and ($C_1$-$C_6$)alkyl-CONH—, or $R^5$ and $R^6$ together with the nitrogen atom to which they are attached form a (4- to 8-membered)heterocycle;

$R^7$ is selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl) -($C_1$-$C_6$)alkyl- ;

$R^9$ and $R^{10}$ are each independently selected from the group consisting of hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, and (($C_3$-$C_{12}$)cycloalkenyl)-($C_1$-$C_6$)alkyl-;

$R^{12}$ and $R^{13}$ are each independently selected from the group consisting of hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(6- to 14-membered)aryl, ((6- to14-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; each of which is optionally substituted with 1 or 2 substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, -NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(6- to 14-membered)aryl, ((6- to 14-membered)aryl) -($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from the group consisting of —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, and ($C_1$-$C_6$)alkyl-CONH—;

G is NR$^{16}$, or O;

X is selected from the group consisting of —($C_1$-$C_{10}$)alkoxy, OH, hydroxy($C_1$-$C_6$)alkyl-, dihydroxy($C_1$-$C_6$)alkyl-, halogen, —NH$_2$, —NR$^2$(C=O)R$^{12}$, —CONR$_{12}$R$^{13}$, Q is selected from the group consisting of OH, —($C_1$-$C_{10}$)alkoxy, —($C_1$-$C_{10}$)alkyl, —O—($C_1$-$C_6$)alkyl, -(6- to 14-membered)aryl, —O—((6- to 14-membered)aryl), ((6- to 14-membered)aryl)-($C_1$-$C_6$)alkyl-, —O—((6- to 14-membered)aryl)- ($C_1$-$C_6$)alkyl, (5- to 12-membered) heteroaryl, —O—((5- to 12-membered)heteroaryl), ((5- to 12-membered)heteroaryl)-($C_1$-$C_6$)alkyl-, and —O— ((5- to 12-membered)heteroaryl-($C_1$-$C_6$)alkyl;

$R^{15a}$ and $R^{16b}$ are each independently selected from the group consisting of:

a) hydrogen, OH;

b) saturated, unsaturated, or partially saturated —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_2$-$C_6$)alkenyl-, (($C_3$-$C_{12}$)cycloalkyl)-($C_1$-$C_6$)alkoxy-;

c) -(6- to 14-membered)aryl, ((6- to 14-membered)aryl)-($C_1$-$C_6$)alkyl-, ((6- to 14-membered)aryl)-($C_1$-$C_6$)alkoxy-, ((6- to 14-membered)aryl) -($C_2$-$C_6$)alkenyl-; or d) -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_2$-$C_6$)alkenyl-; and e) -(3- to 12-membered)heterocycle, ((3- to 12-membered)heterocycle)- ($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle) - ($C_1$-$C_6$)alkyl-, and ((7- to 12-membered)bicycloheterocycle)-($C_1$-$C_6$)alkoxy-;

provided that at least one of $R^{15a}$ and $R^{16b}$ is other than hydrogen;

$R^{16}$ is selected from hydrogen and —($C_1$-$C_6$)alkyl;

Y is —(CH$_2$)$_n$—CH;

n is an integer 0, 1, 2, 3, 4, 5 or 6;

s is an integer 1, 2, 3, 4, 5, 6, 7, 8, 9, 10, 11, 12, or 13;

or a pharmaceutically acceptable salt, or solvate thereof.

2. A compound of claim 1 having Formula II:

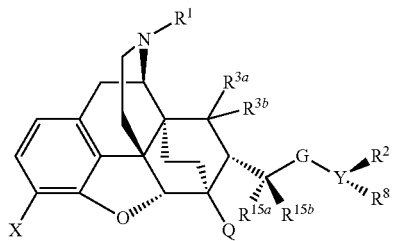
(II)

wherein $R^1$, $R^2$, $R^{3a}$, $R^{3b}$, $R^8$, $R^{15a}$, $R^{15b}$, Q and X are as defined above for Formula I, or a pharmaceutically acceptable salt or solvate thereof.

3. A compound of claim 1 having Formula III:

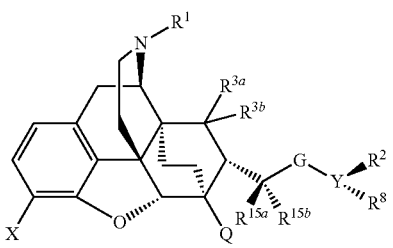
(III)

wherein $R^1$, $R^2$, $R^{3a}$, $R^{3b}$, $R^8$, $R^{15a}$, $R^{15b}$, Q and X are as defined above for Formula I, or a pharmaceutically acceptable salt or solvate thereof.

4. A compound of claim 1 having Formula IV:

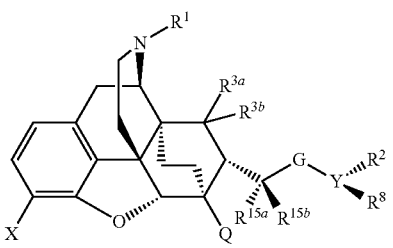
(IV)

wherein $R^1$, $R^2$, $R^{3a}$, $R_{3b}$, $R^8$, $R^{15a}$, $R^{15b}$, Q and X are as defined above for Formula I, or a pharmaceutically acceptable salt or solvate thereof.

5. A compound of claim 1 having Formula V:

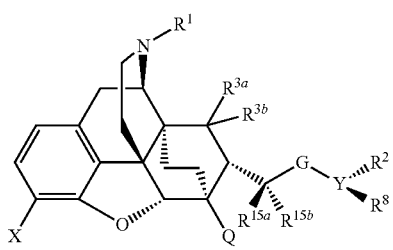
(V)

wherein $R^1$, $R^2$, $R^{3a}$, $R^{3b}$, $R^8$, $R^{15a}$, $R^{15b}$, Q and X are as defined above for Formula I, or a pharmaceutically acceptable salt or solvate thereof.

6. The compound of claim 1, wherein G is $NR^{16}$.

7. The compound of claim 6, wherein $R^{16}$ is hydrogen.

8. The compound of claim 1, wherein G is O.

9. The compound of claim 1, wherein at least one of $R^{15a}$ and $R^{15b}$ is -(6- to 14-membered)aryl.

10. The compound of claim 9, wherein at least one of $R^{15a}$ and $R^{15b}$ is phenyl.

11. The compound of claim 1, wherein at least one of $R^{15a}$ and $R^{15b}$ is (6- to 14-membered)aryl-$(C_1$-$C_6)$alkyl-.

12. The compound of claim 11, wherein at least one of $R^{15a}$ and $R^{15b}$ is benzyl.

13. The compound of claim 1, wherein one of $R^{15a}$ and $R^{15b}$ is hydrogen.

14. The compound of claim 1, wherein at least one of $R^{15a}$ and $R^{15b}$ is OH.

15. The compound of claim 1, wherein at least one of $R^2$ and $R^8$ is —$(C_1$-$C_{10})$alkyl.

16. The compound of claim 1, wherein at least one of $R^2$ and $R^8$ is —$(C_1$-$C_{10})$alkyl substituted with —$COOR^7$.

17. The compound of claim 16, wherein $R^7$ is hydrogen.

18. The compound of claim 1, wherein at least one of $R^2$ and $R^8$ is —$(C_1$-$C_{10})$alkyl substituted with —$CONR^5R^6$.

19. The compound of claim 18, wherein $R^5$ and $R^6$ are both hydrogen.

20. The compound of claim 1, wherein at least one of $R^2$ and $R^8$ is -(6- to 14-membered)aryl.

21. The compound of claim 20, wherein at least one of $R^2$ and $R^8$ is phenyl.

22. The compound of claim 1, wherein at least one of $R^2$ and $R^8$ is (6- to 14-membered)aryl-$(C_1$-$C_6)$alkyl-.

23. The compound of claim 22, wherein at least one of $R^2$ and $R^8$ is benzyl.

24. The compound of claim 1, wherein at least one of $R^2$ and $R^8$ is $COOR^7$.

25. The compound of claim 1, wherein $R^2$ is $COOR^7$ and $R^8$ is -(6- to 14-membered)aryl.

26. The compound of claim 1, wherein $R^1$ is cyclopropylmethyl.

27. The compound of claim 1, wherein X is —$(C_1$-$C_{10})$alkoxy.

28. The compound of claim 27, wherein X is methoxy.

29. The compound of claim 27, wherein X is ethoxy.

30. The compound of claim 1, wherein X is OH.

31. The compound of claim 1, wherein Q is —$(C_1$-$C_{10})$alkoxy.

32. The compound of claim 31, wherein Q is methoxy.

33. The compound of claim 31, wherein Q is ethoxy.

34. The compound of claim 1, wherein Q is OH.

35. The compound of claim 1, wherein Y is CH.

36. The compound of claim 1, wherein Y is CH, $R^8$ is -(6- to 14-membered)aryl, and $R^2$ is $COOR^7$.

37. The compound of claim 1, wherein Y is CH, $R^8$ is (6- to 14-membered)aryl-$(C_1$-$C_6)$alkyl-, and $R^2$ is $COOR^7$.

38. The compound of claim 1, wherein Y is CH, $R^8$ is -(6- to 14-membered)aryl, and $R^2$ is -$(C_1$-$C_{10})$alkyl substituted with —CON R5R6.

39. The compound of claim 1, wherein Y is CH, $R^8$ is (6- to 14-membered)aryl-$(C_i$-$C_6)$alkyl-, and $R^2$ is —$(C_1$-$C_{10})$alkyl substituted with —$CONR^5R^6$.

40. The compound of claim 1, wherein at least one of $R^2$ and $R^8$ is -(6- to 14-membered)aryl, and at least one of $R^{15a}$ and $R^{15b}$ is -(6- to 14-membered)aryl.

41. The compound of claim 1, wherein at least one of $R^2$ and $R^8$ is (6- to 14-membered)aryl-($C_1$-$C_6$)alkyl-, and at least one of $R^{15a}$ and $R^{15b}$ is -(6- to 14-membered)aryl.

42. The compound of claim 1, wherein at least one of $R^2$ and $R^8$ is -(6- to 14-membered)aryl, and at least one of $R^{15a}$ and $R^{15b}$ is (6- to 14-membered)aryl-($C_1$-$C_6$)alkyl-.

43. The compound of claim 1, wherein at least one of $R^2$ and $R^8$ is (6- to 14-membered)aryl-($C_1$-$C_6$)alkyl-, and at least one of $R^{15a}$ and $R^{15b}$ is (6- to 14-membered)aryl-($C_1$-$C_6$)alkyl-.

44. A compound selected from the group consisting of:

2-(((S)-((4 R,4 aS,6 R,7 R,7 aR,12 bS)-3-(cyclopropylmethyl)-7,9-dimethoxy-1,2,3,4,5,6,7,7 a-octahydro-4 a,7-ethano-4,12-methanobenzofuro[3,2-e]isoquinolin-6-yl)(phenyl)methyl)amino)acetic acid (Compound 12);

2-(((S)-((4 R,4 aS,6 R,7 R,7 aR,12 bS)-3-(cyclopropylmethyl)-7,9-dimethoxy-1,2,3,4,5,6,7,7 a-octahydro-4 a,7-ethano-4,1 2-methanobenzofuro[3,2-e ]isoquinolin-6-yl)(phenyl)methyl)amino)propanoic acid (Compound 13);

2-(((S)-((4 R,4 aS,6 R,7 R,7 aR,12 bS)-3-(cyclopropylmethyl)-7,9-dimethoxy-1,2,3,4,5,6,7,7 a-octahydro-4 a,7-ethano-4,1 2-methanobenzofuro[3,2-e]isoquinolin-6-yl)(phenyl)methyl)amino)-2-phenylacetic acid (Compound 15);

2-(((S)-((4 R,4 aS,6 R,7 R,7 aR,12 bS)-3-(cyclopropyl methyl)-7,9-di methoxy-1,2,3,4,5,6,7,7 a-octahydro-4 a,7-ethano-4,1 2-methanobenzofuro[3,2-e ]isoquinolin-6-yl)(phenyl)methypamino)propanamide (Compound 14);

(R)-2-(((S)-((4 R,4 aS,6 R,7 R,7 aR,12 bS)-3-(cyclopropyl methyl)-7,9-di methoxy-1,2,3,4,5,6,7,7 a-octahydro-4 a,7-ethano-4,1 2-methanobenzofuro[3,2-e ]isoquinolin-6-yl)(phenyl)methypamino)-2-phenylacetamide (Compound 16); and (S)-2-(((S)-((4 R,4 aS,6 R,7 R,7 aR,12 bS)-3-(cyclopropyl methyl)-7,9-di methoxy-1,2,3,4,5,6,7,7 a-octahydro-4 a,7-ethano-4,1 2-methanobenzofuro[3,2-e ]isoquinolin-6-yl)(phenyl)methypamino)-2-phenylacetamide (Compound 17); and the pharmaceutically acceptable salts and solvates thereof.

45. A pharmaceutical composition comprising an effective amount of a compound of claim 1, or a pharmaceutically salt or solvate thereof, and a pharmaceutically acceptable carrier or excipient.

46. A method of treating pain in a mammal, comprising administering to such mammal in need thereof an effective amount of a compound of claim 1, or a pharmaceutically acceptable salt or solvate thereof.

47. A method for preparing a composition, comprising the step of admixing a compound according to claim 1, or a pharmaceutically acceptable salt or solvate thereof, with a pharmaceutically acceptable carrier or excipient.

* * * * *